United States Patent
Speckbacher et al.

(10) Patent No.: US 12,122,734 B2
(45) Date of Patent: Oct. 22, 2024

(54) TELESCOPING SYNTHESES OF 2-METHOXYMETHYL-P-PHENYLENEDIAMINE

(71) Applicant: Wella Germany GmbH, Darmstadt (DE)

(72) Inventors: Markus Speckbacher, Darmstadt (DE); Armin Osan, Darmstadt (DE); Heike Abel, Darmstadt (DE); Gerd Schlotzhauer, Darmstadt (DE)

(73) Assignee: WELLA GERMANY GMBH, Darmstadt (DE)

( * ) Notice: Subject to any disclaimer, the term of this patent is extended or adjusted under 35 U.S.C. 154(b) by 195 days.

(21) Appl. No.: 17/633,163

(22) PCT Filed: Aug. 12, 2020

(86) PCT No.: PCT/EP2020/072678
§ 371 (c)(1),
(2) Date: Feb. 4, 2022

(87) PCT Pub. No.: WO2021/028506
PCT Pub. Date: Feb. 18, 2021

(65) Prior Publication Data
US 2022/0298101 A1    Sep. 22, 2022

Related U.S. Application Data

(60) Provisional application No. 62/886,012, filed on Aug. 13, 2019.

(51) Int. Cl.
*C07C 213/02* (2006.01)
*C07C 46/00* (2006.01)

(52) U.S. Cl.
CPC .......... *C07C 213/02* (2013.01); *C07C 46/00* (2013.01)

(58) Field of Classification Search
CPC ...... C07C 213/04; C07C 46/00; C07C 213/02
See application file for complete search history.

(56) References Cited

U.S. PATENT DOCUMENTS

2012/0142969 A1    6/2012    Gardlik

OTHER PUBLICATIONS

N. Singh, et.al. 197, Hyperfine Interact 309-315 (2010)("Singh") (Year: 2010).*
K. O'Shea, et.al. 113, J. Am. Chem. Soc. 611-615 (1991)("O'Shea") (Year: 1991).*
N. Jacobsen, et al. 763, Justus Liebigs Annalen der Chemie, 135-147 (1972) (Year: 1972).*
R. Mohrig, et al. Techniques in organic chemistry. Macmillan (2010) (Year: 2010).*
International Search Report issued in connection with PCT Application No. PCT/EP2020/072678 dated Oct. 12, 2020.

* cited by examiner

*Primary Examiner* — Alexander R Pagano
*Assistant Examiner* — Frank S. Hou
(74) *Attorney, Agent, or Firm* — Dennemeyer & Associates LLC; Victoria Friedman

(57) ABSTRACT

The invention relates to processes for preparing 2-methoxymethyl-p-phenylenediamine (I), cosmetically acceptable salts thereof, or mixtures thereof.

4 Claims, No Drawings

TELESCOPING SYNTHESES OF 2-METHOXYMETHYL-P-PHENYLENEDIAMINE

CROSS-REFERENCE TO RELATED APPLICATIONS

This is a 35 U.S.C. 371 National Stage Patent Application of International Application No. PCT/EP2020/072678, filed Aug. 12, 2020, which claims priority to U.S. Provisional Application No. 62/886,012, filed Aug. 13, 2019, each of which is hereby incorporated by reference in its entirety.

FIELD OF THE INVENTION

The present invention relates to a new telescoping synthesis of 2-methoxymethyl-p-phenylenediamine according to formula (I) or salts thereof. This compound is known to the industry as low sensitizing major dye precursor used in oxidative hair dye compositions as replacement for traditional p-phenylenediamine or p-toluenediamine dye precursors

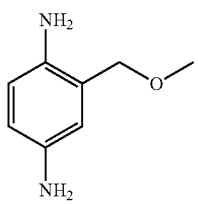

[I]

BACKGROUND OF THE INVENTION p-phenylenediamine derivatives are key precursors for oxidative hair dyeing. They are usually used to generate dark shades. p-phenylenediamine derivatives have been used for decades for hair dyeing. Among the p-phenylenediamine derivatives, a particularly favourable candidate, namely 2-methoxymethyl-p-phenylenediamine has been identified. This dye precursor is particularly advantageous in that it is typically characterised by a lower sensitizing potential than traditional p-phenylenediamine or p-toluenediamine dye precursors.

In the past, the industry already published different synthetic routes to manufacture 2-methoxymethyl-p-phenylenediamine (I) or salts thereof.

For example, US2003/0041392A1 discloses a process for the preparation of 2-methoxymethyl-p-phenylenediamine (I) via a Smiles rearrangement in one of the intermediate steps. Disadvantages of the process are harsh reaction conditions and the use of reactants such as trioxane (formaldehyde trimer) which may create health hazards for the workers in the production line. In addition, the process produces large amounts of waste solvent solutions containing sulfuric acid or toluoyl. These solutions cannot be recycled for the process but have to be discarded. Yields for the process according to US2003/0041392A1 are in the order of 50% of theoretical.

Another possible synthetic route has been disclosed in WO2012044758A1. This synthetic route comprises a combination of steps starting with 2-chlorobenzylchloride and methanol to form the methoxymethyl intermediate. Nitration occurs in 4 position and activates the chloride as leaving group. Substitution of the chloride by an amino donor, preferably using benzylamine, requires a phase-transfer catalyst to obtain the aniline intermediate. Final hydrogenation leads to the desired 2-methoxymethyl-p-phenylenediamine. Disadvantages of this method include harsh nitrosation conditions (using mixtures of sulfuric acid and fuming nitric acid), and an overall yield that may be relatively low. Furthermore, the carbon balance is insufficient, since the reactant benzylamine merely contributes a nitrogen atom, while the remainder of the molecule is discarded in the form of toluene-containing mixtures. A particular disadvantage of this method is that the product obtained comprises amorphous material which may lead to unwanted side effects such as surface oxidation. Surface oxidation in turn may negatively impact the appearance of the powdered material which can be a success criteria for cosmetic applications/formulations.

Therefore, there still exists the need to provide a new process for preparing 2-methoxymethyl-2-phenylenediamine (1), a cosmetically acceptable salt thereof, or mixture thereof which is particularly cost effective versus other published and commercialized methods. In regard of an increasing demand, an economical access to 2-methoxymethyl-2-phenylenediamine (I) would be appreciated. This manufacturing process should also be able to provide material with a low impurity level in accordance with global regulations. Furthermore, the process should also reduce the risk of non-controllable side reactions and involve inexpensive starting materials and use more standardized chemical reactions versus known processes which are regarded state of the art. Finally, in view of increasing ecological demands, manufacturers should be able to conduct the process under mild reaction conditions, involving moderate temperatures, using ecologically acceptable solvents, and producing a minimum of non-recyclable waste solutions.

It has surprisingly now been found, that new synthesis pathways starting with readily commercially available feedstock materials, will lead to the desired 2-methoxymethyl-2-phenylenediamine (1) with enhanced economics and significantly decreased use of organic solvents versus the current state of the art. The synthesis routes presented herein may use water and aqueous solutions in one or more steps of the reaction course and therefore may replace expensive and environmentally problematic organic solvents used in previously described synthesis methods for the preparation of 2-methoxymethyl-2-phenylenediamine (1).

SUMMARY OF THE INVENTION

Subject matter of the present invention is a process for preparing 2-methoxymethyl-p-phenylenediamine (I), a cosmetically acceptable salt thereof, or mixture thereof.

The process, depicted in Reaction Scheme 1 below, comprises:
(a) providing 2-methoxymethyl-1,4-benzochinone (IV);
(b) condensing 2-methoxymethyl-1,4-benzochinone (IV) with an amine source NH2R1 to form 2-(methoxymethyl)-N1(R1),N4(R1)-cyclohexa-2,5-diene-1,4-diimine (Va); and
(c) reacting 2-(methoxymethyl)-N1(R1),N4(R1)-cyclohexa-2,5-diene-1,4-diimine (Va) in the presence of a hydrogen source to form 2-methoxymethyl-p-phenylenediamine (I).

Reaction Scheme 1a

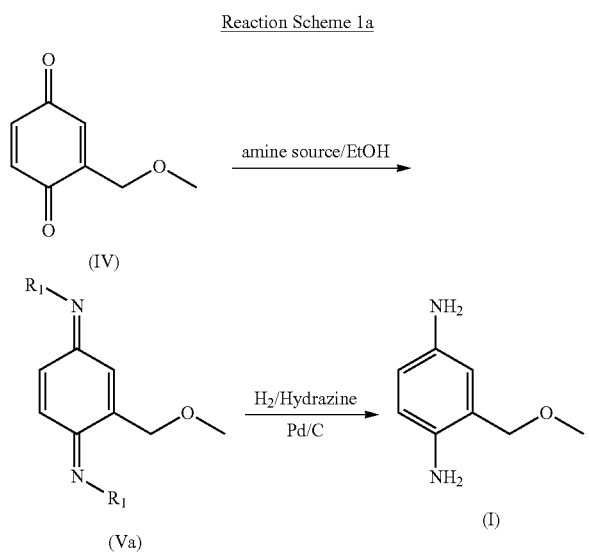

The amine source NH2-R1 comprises a primary amine group. The moiety R1 is selected from OH, NH2, linear or branched (C1-C6)alkyl which optionally may be substituted with OH, linear or branched (C1-C6)alkylene-(C5-C6)cycloalkyl and linear or branched (C1-C6)alkylbenzol, Condensation of 2-methoxymethyl-1,4-benzochinone (IV) with the amine source to form 2-(methoxymethyl)-N1 (R1),N4(R1)-cyclohexa-2,5-diene-1,4-diimine (Va) can be done, for example, in ethanol. Hydrogenation conveniently is carried out in the presence of a hydrogen source such as hydrogen or hydrazine, for example, typically in the presence of a catalyst, for example a metal catalyst such as Pd/C.

According to a particular embodiment, step (b) is carried out by condensing 2-methoxymethyl-1,4-benzochinone (IV) with hydroxylamine NH2OH to form the corresponding bis-oxime 2-(methoxymethyl)-cyclohexa-2,5-diene-1,4-dione oxime (Vb), as depicted below in Reaction Scheme 1b.

Reaction Scheme 1b

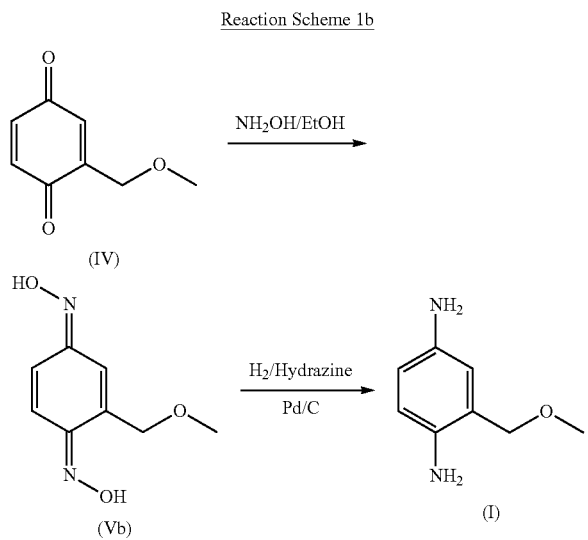

As with the general reaction with an amine source, the condensation reaction with hydroxylamine may be conducted, for example, in ethanol. Hydrogenation conveniently is carried out in the presence of a hydrogen source such as hydrogen or hydrazine, for example, typically in the presence of a catalyst, for example a metal catalyst such as Pd/C.

The process may further comprise the step of preparing the starting compound 2-methoxymethyl-1,4-benzochinone (IV).

According to one embodiment, depicted in Reaction Scheme 2 below, the step of preparing 2-methoxymethyl-1, 4-benzochinone (IV) comprises the steps of:

(a1) alkylating 1,4-benzoquinone (VIII) in the presence of 2-methoxyacetic acid (IX) to form a mixture of 2-methoxymethyl-1,4-benzochinone (IV) and 1,4-benzoquinone (VIII); and (a2) removing 1,4-benzoquinone (VIII).

Reaction Scheme 2

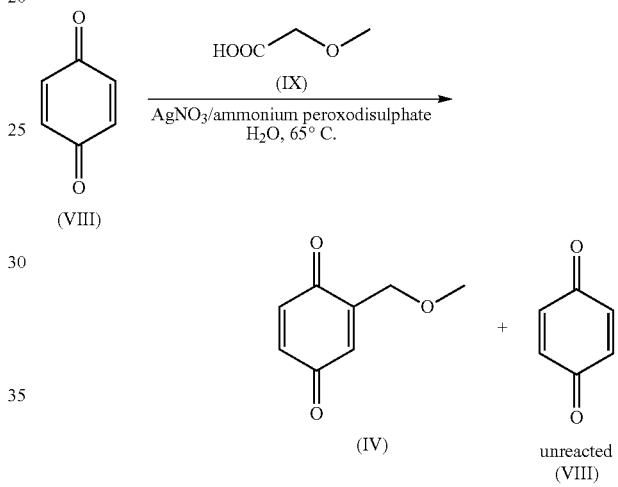

Radical alkylation of 1,4-benzoquinone (VIII) with 2-methoxyacetic acid (IX) to form 2-methoxymethyl-1,4-benzochinone (IV) may be done, for example, in the presence of silver nitrate and ammonium peroxodisulphate as radical former. The reaction may be carried out in aqueous solution, such as for example in water. The transformation rate is about 45%, hence unreacted 1,4-benzoquinone (VIII) is still present in the reaction mixture, beside some detectable di-alkylated byproducts, after the alkylation is complete. Removing the unreacted 1,4-benzoquinone (VIII) can be realized via water steam distillation, thin film distillation/evaporation, short path distillation/evaporation or slow sublimation from aqueous solution, after the completion of alkylating step to separately isolate the 1,4-benzoquinone (VIII) from the reaction mixture. Furthermore, the unreacted 1,4-benzoquinone (VIII) can be recovered with no loss and can be used for the next reaction course to further improve the profitability of the process.

According to another embodiment, depicted in Reaction Scheme 3 below, the step of preparing 2-methoxymethyl-1, 4-benzochinone (IV) comprises the steps of:

(a3) providing 2-methyl-1,4-benzochinone (II);

(a4) brominating 2-methyl-1,4-benzochinone (II) to form 2-bromomethyl-1,4-benzochinone (III); and (a5) etherifying 2-bromomethyl-1,4-benzochinone (III) to form 2-methoxymethyl-1,4-benzochinone (IV).

Reaction Scheme 3

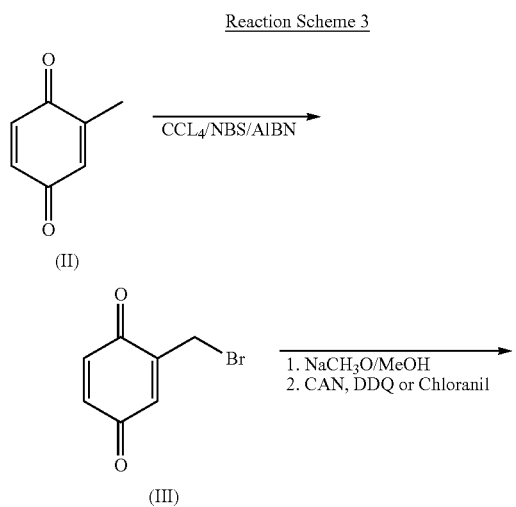

(AIBN) as radical starter. While activation of (II) by chlorination might be possible, bromination is used routinely.

Etherification of 2-bromomethyl-1,4-benzochinone (III) to form 2-methoxymethyl-1,4-benzochinone (IV) in CH3OH/CH3O⁻ is a spontaneous reaction occurring at room temperature (18-25° C.). Optionally, the etherification reaction may be supported by the presence of a mild oxidation agent such as CAN, DDQ or Chloranil. The presence of an oxidizing agent at this stage aids in avoiding potential rearomatization, thereby increasing the overall yield of (IV).

According to still another embodiment, depicted in Reaction Scheme 4 below, the step of preparing 2-methoxymethyl-1,4-benzochinone (IV) comprises the steps of:

(a6) providing 1,4-dimethoxy-2-methyl-benzene (VI);

(a7) brominating 1,4-dimethoxy-2-methyl-benzene (VI) to form 2(bromomethyl)-1,4-dimethoxy-benzene (VIIa);

(a8) etherifying 2(bromomethyl)-1,4-dimethoxy-benzene (VIIa) to form 1,4-dimethoxy-2-(methoxymethyl)benzene (VIIb); and (a9) oxidizing 1,4-dimethoxy-2-(methoxymethyl)benzene (VIIb) to form 2-methoxymethyl-1,4-benzochinone (IV).

Reaction Scheme 4

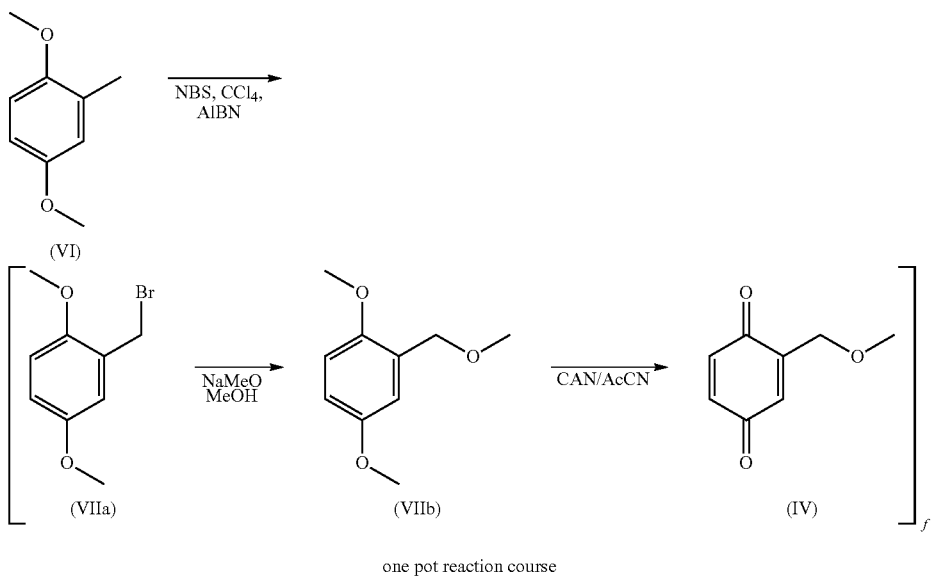

-continued

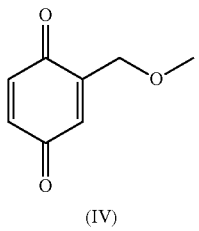

(IV)

Bromination of 2-methyl-1,4-benzochinone (II) to form 2-bromomethyl-1,4-benzochinone (III) typically is carried out under reflux conditions, using for example carbon tetrachloride as solvent. N-Bromo-succinimide (NBS) is conveniently used for the bromination, with azo-iso-butyronitril Reaction conditions and reactants for the halogenation, in particular bromination, and for the etherification are as indicated above in the context of Reaction Scheme 3. Oxidation of 1,4-dimethoxy-2-(methoxymethyl)benzene (VIIb) to form 2-methoxymethyl-1,4-benzochinone (IV) may be accomplished, for example, with CAN (ceric ammonium nitrate) in acetonitrile.

According to still another embodiment, depicted in Reaction Scheme 5 below, the step of preparing 2-methoxymethyl-1,4-benzochinone (IV) comprises the steps of:

(a10) methylating 3-(hydroxymethyl)phenol (XIX) to form 3-(methoxymethyl)phenol (XX); and (a11) oxidizing 3-(methoxymethyl)phenol (XX) to form 2-methoxymethyl-1,4-benzochinone (IV).

Reaction Scheme 5

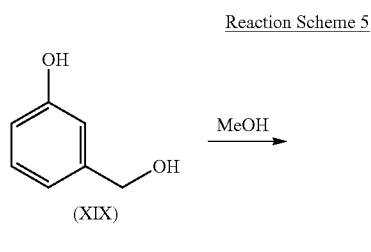

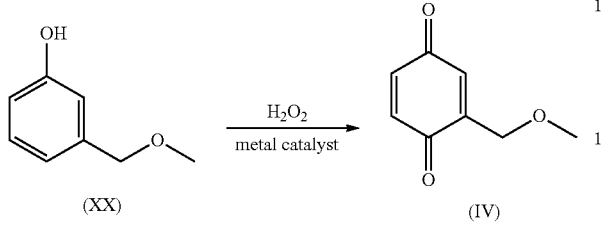

The methylation of 3-(hydroxymethyl)phenol (XIX) (alternatively (3-methoxyphenyl)methanol) to form 3-(methoxymethyl)phenol (XX) may be carried out, for example, with dimethylsulphate in methanol. Alternatively, it might be possible to accomplish the methylation of (XIX) to form (XX) in methanol under pressure. The subsequent oxidation of 3-(methoxymethyl)phenol (XX) to obtain 2-methoxymethyl-1,4-benzochinone (IV) may be done, for example, using hydrogen peroxide, typically in the presence of a catalyst, for example a metal catalyst such as e.g. titanium superoxide or tungsten/molebdenum complexes.

According to another embodiment, the process for preparing 2-methoxymethyl-p-phenylenediamine (I), a cosmetically acceptable salt thereof, or mixture thereof comprises the following steps:
- (a1) alkylating 1,4-benzoquinone (VIII) in the presence of 2-methoxyacetic acid (IX) to form a mixture of 2-methoxymethyl-1,4-benzochinone (IV) and 1,4-benzoquinone (VIII);
- (b1) in the mixture obtained in step (a1), condensing 2-methoxymethyl-1,4-benzochinone (IV) and 1,4-benzoquinone (VIII) with an amine source NH2-R1 to form 2-(methoxymethyl)-N1(R1),N4(R1)-cyclohexa-2,5-diene-1,4-diimine (Va) and N1(R1),N4(R1)-cyclohexa-2,5-diene-1,4-diimine (Xa);
- (b2) in the mixture obtained in step (b1), oxidizing 2-(methoxymethyl)-N1(R1),N4(R1)-cyclohexa-2,5-diene-1,4-diimine (Va) and N1(R1),N4(R1)-cyclohexa-2,5-diene-1,4-diimine (Xa) to form a mixture of 2-(methoxymethyl)-1,4-dinitroso-benzene (XII) and 1,4-dinitroso-benzene (XIII);
- (b3) isolating 2-(methoxymethyl)-1,4-dinitroso-benzene (XII), and isolating 1,4-dinitroso-benzene (XIII);
- (c1) reacting 2-(methoxymethyl)-1,4-dinitroso-benzene (XI) in the presence of a hydrogen source to form 2-methoxymethyl-p-phenylenediamine (I); and
- (c2) reacting 1,4-dinitroso-benzene (XIII) in the presence of a hydrogen source to form p-phenylenediamine (XI).

The amine source NH2-R1 comprises a primary amine group. The moiety R1 is selected from OH, NH2, linear or branched (C1-C6)alkyl which optionally may be substituted with OH, linear or branched (C1-C6)alkylene-(C5-C6)cycloalkyl and linear or branched (C1-C6)alkylbenzol.

According to a preferred embodiment of the above process, depicted in Reaction Scheme 6 below, the amine source used in step (b1) is hydroxylamine NH2OH, thereby forming a mixture of his-oxime 2-(methoxymethyl)-cyclohexa-2,5-diene-1,4-dione oxime (Vb) and cyclohexa-2,5-diene-1,4-dione oxime (Xb), which mixture of (Vb) and (Xb) is oxidized in subsequent step (b2) to form the mixture of 2-(methoxymethyl)-1,4-dinitroso-benzene (XII) and 1,4-dinitroso-benzene (XIII):

Reaction Scheme 6

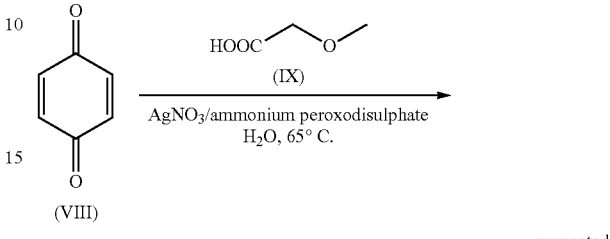

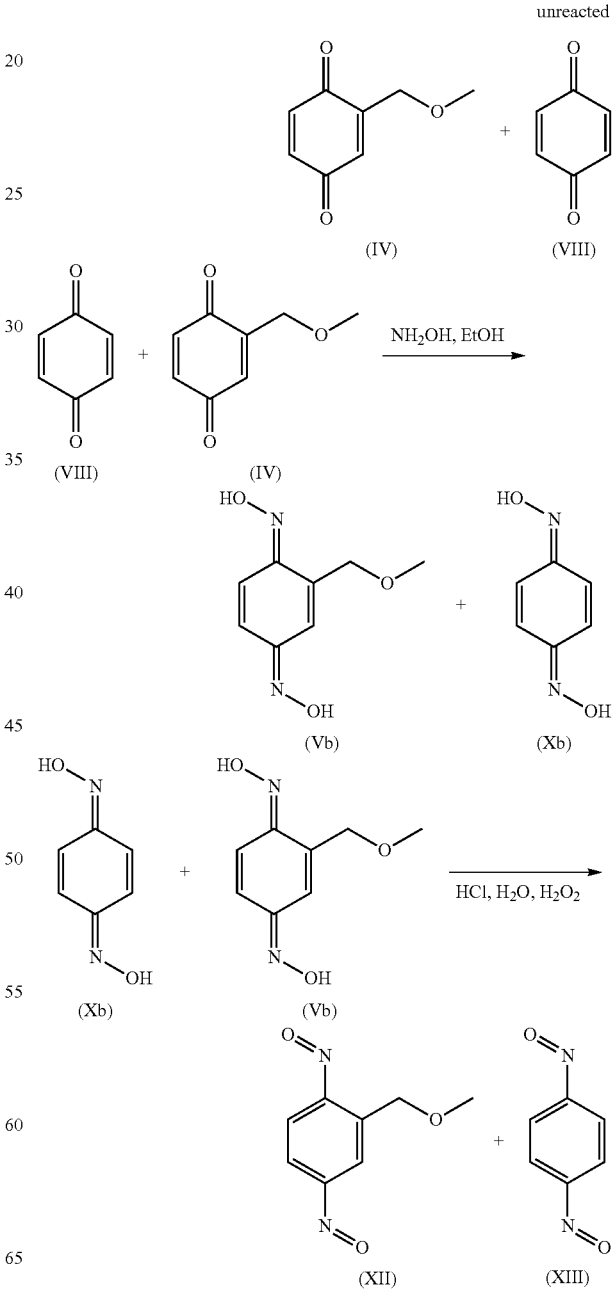

-continued

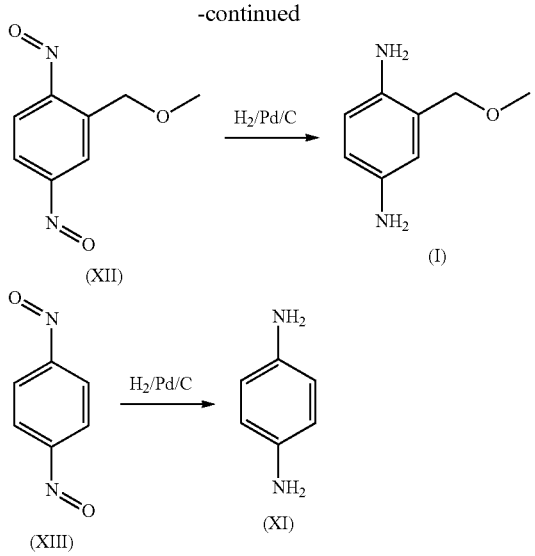
(XII) (I)

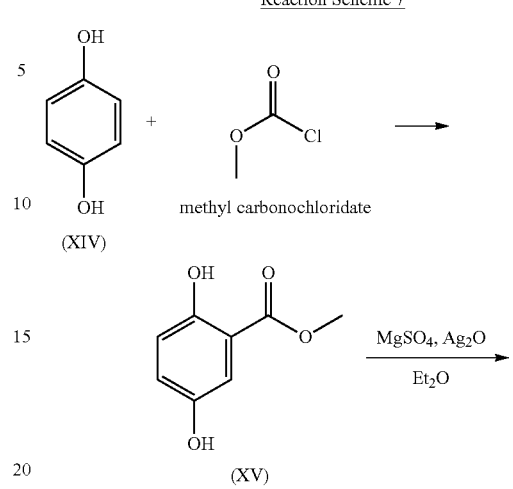
(XIII) (XI)

As disclosed above in the context of Reaction Scheme 2, 1,4-benzoquinone (VIII) is radically alkylated with 2-methoxyacetic acid (IX). Deviating from Reaction Scheme 2 above, however, the unreacted 1,4-benzoquinone (VIII) still present in the reaction mixture is not removed according to the process depicted in Reaction Scheme 6. Rather, the mixture of 1,4-benzoquinone (VIII) and 2-methoxymethyl-1,4-benzochinone (IV) is converted to the corresponding bis-oximes 2-(methoxymethyl)-cyclohexa-2,5-diene-1,4-dione oxime (Vb) and cyclohexa-2,5-diene-1,4-dione oxime (Xb) via condensation of hydroxylamine. Subsequently, conversion of (Vb) and (Xb) into the tautomeric bis-nitroso compounds (XII) and (XIII) may be done, for example, via smooth oxidation in hydrochloric acid with hydrogen peroxide. Elimination of byproducts and subsequent separation of compounds (XII) and (XIII) may be accomplished, for example, via recrystallization or vacuum distillation. The final hydrogenation step provides the desired 2-methoxymethyl-p-phenylenediamine (I) and, from the same reaction course, the commercially interesting p-phenylene-diamine (XI) in comparable yields.

Further subject matter of the present invention is a process for preparing 2-methoxymethyl-p-phenylenediamine (I), a cosmetically acceptable salt thereof, or mixture thereof as depicted in Reaction Scheme 7 below. The process comprises the following steps:

(i) acylating p-hydrochinone (XIV) with methyl-chlorformiate to form methyl 2,5-dihydroxybenzoate (XV);
(ii) oxidizing methyl 2,5-dihydroxybenzoate (XV) to form methyl 3,6-dioxocyclohexa-1,4-diene-1-carboxylate (XVI);
(iii) condensing methyl 3,6-dioxocyclohexa-1,4-diene-1-carboxylate (XVI) with hydroxylamine NH2OH to form bis-oxime (3Z,6E)-3,6-bis(hydroxyimino)cyclohexa-1,4-diene-1-carboxylic acid (XVII);
(iv) converting of bis-oxime (3Z,6E)-3,6-bis(hydroxyimino)cyclohexa-1,4-diene-1-carboxylic acid (XVII) into the corresponding thionoester (XVIII); and
(v) hydrogenating thionoester (XVIII) in the presence of a hydrogen source to form 2-methoxymethyl-p-phenylenediamine (I).

Reaction Scheme 7

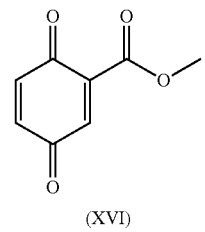
(XIV) methyl carbonochloridate (XV)

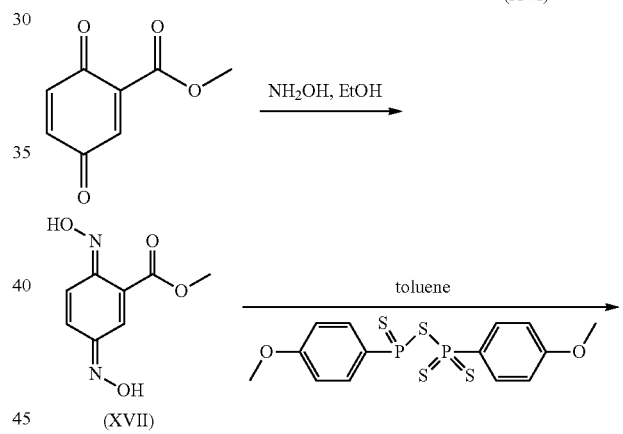
(XVI)

(XVII)

(XVIII)

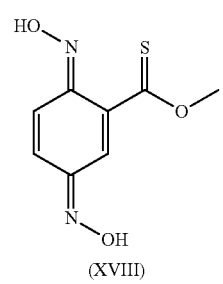
(XVIII)

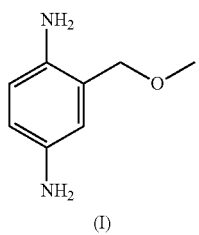

(I)

The acylation of p-hydrochinone (XIV) to form methyl 2,5-dihydroxybenzoate (XV) is carried out using methylchlorformiate, typically at room temperature or mildly elevated temperatures. Methyl 2,5-dihydroxybenzoate (XV) then is oxidized to form methyl 3,6-dioxocyclohexa-1,4-diene-1-carboxylate (XVI), followed by condensation of (XVI) with hydroxylamine NH2OH to form bis-oxime (3Z, 6E)-3,6-bis(hydroxyimino)cyclohexa-1,4-diene-1-carboxylic acid (XVII). The condensation may be carried out in an alcoholic medium such as ethanol. Conversion of (XVII) into the corresponding thionoester (XVIII) may be accomplished for example via $P_4O_{10}$ or Lawsson's reagent in an organic solvent such as toluene, followed by hydrogenation of thionoester (XVIII) in the presence of a hydrogen source (such as hydrazine), typically in the presence of a metal catalyst (such as Raney nickel), to form the desired end-product 2-methoxymethyl-p-phenylenediamine (I).

DETAILED DESCRIPTION OF THE INVENTION

The sequence of steps, including all identified intermediates, involved in the telescoping synthesis and large scale process, is described in detail in the following. It is to be understood that when the present disclosure refers to a particular structure, all of the reasonable additional tautomeric structures are included. In the art tautomeric structures are frequently represented by one single structure and the present disclosure follows this general practice.

It is to be understood that the steps described to prepare 2-methoxymethyl-p-phenylenediamine according to formula (I) may be performed in a sequential one-pot synthesis, with reagents added to a reactor one at a time and without work-up in between. The reaction steps require suitable solvents, as indicated below. Sequential one-pot synthesis without work-up in between is preferred, unless it is preferred to avoid by-products from a preceding step in a subsequent step.

The present invention relates to a telescoping process for the preparation of 2-methoxymethyl-p-phenylenediamine of formula (I), a cosmetically acceptable salt thereof, or mixture thereof comprising the steps as described accordingly hereinafter.

A Synthesis of 2-methoxymethyl-p-phenylenediamine (I) Using 2-methoxymethyl-1,4-benzochinone (IV) as Starting Material Reaction Scheme 1a

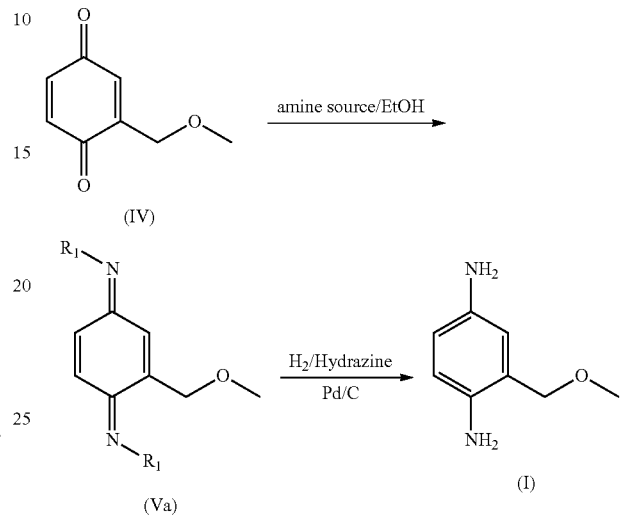

2-Methoxymethyl-1,4-benzochinone (IV) is dissolved in a suitable solvent such as ethanol, heated to reflux in the presence of a base, preferable calcium carbonate and reacted with an amine source NH2-R1, wherein R1 is selected from OH, NH2, linear or branched (C1-C6)alkyl which optionally may be substituted with OH, linear or branched (C1-C6) alkylene-(C5-C6)cycloalkyl and linear or branched (C1-C6) alkylbenzol to form 2-(methoxymethyl)-N1(R1),N4(R1)-cyclohexa-2,5-diene-1,4-diimine (Va).

For example, when using hydrazine hydrate as the amine source the corresponding chinone hydrazine derivative is obtained as diimine derivative (Va), as depicted in Reaction Scheme 8 below.

Reaction Scheme 8

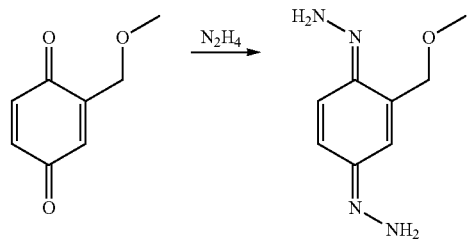

Hydroxylamine NH2OH is preferably used as the amine source NH2-R1, followed by hydrazine NH2-NH2, and the alkylamines starting with methylamine in increasing order.

According to a particular embodiment, 2-methoxymethyl-1,4-benzochinone (IV) is condensed with 3 equivalents hydroxylamine to form the corresponding bis-oxime 2-(methoxymethyl)-cyclohexa-2,5-diene-1,4-dione oxime (Vb).

Reaction Scheme 1b

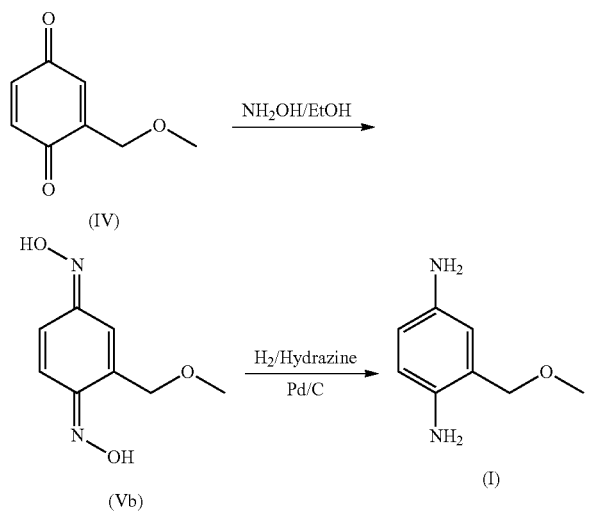

Condensation of 2-methoxymethyl-1,4-benzochinone (IV) with 3 equivalents of hydroxylamine in ethanol in the presence of a base yields the corresponding bis-oxime 2-(methoxymethyl)-cyclohexa-2,5-diene-1,4-dione oxime (Vb). The base may be selected from calcium carbonate, sodium carbonate, potassium carbonate, sodium acetate, DBU, DBN, Huenig Base, ammonium sulphate, sodium hydrogencarbonate and potassium hydrogencarbonate. According to an embodiment, calcium carbonate is used as the base.

After the conversion to the diamine derivative or bis-oxime derivative is completed, the respective intermediate is filtered and the solvent gently removed in vacuum at a possible low temperature (<50° C.). Purification can be carried out via recrystallization to eliminate traces of impurities still present. Solvents for the recrystallization may be selected from the group of 1,2-dimethoxyethane, ethyl acetate, pentane, cyclopentane, hexane, cyclohexane, benzene, toluene, 1,4-dioxane, diethyl ether, tetrahydrofuran, methyl-tetrahydrofuran, n-pentanol, n-butanol, acetic acid, propionic acid, oxalic acid, malonic acid, sulphuric acid, phosphoric acid, iso-pentanol, t-butanol, isopropanol, n-propanol, ethanol, methanol, glycols, hydrogen chloride, water and mixtures thereof. Preferably, the solvent for the recrystallization may be selected from the group consisting of n-butanol, isopropanol, n-propanol, ethanol, methanol, acetic acid, propionic acid, oxalic acid, malonic acid, hydrogen chloride, sulphuric acid, phosphoric acid and mixtures thereof. In particular, the solvent for the recrystallization may be selected from the group consisting of n-propanol, acetic acid, propionic acid, oxalic acid, malonic acid, hydrogen chloride, sulphuric acid, phosphoric acid and mixtures thereof.

Hydrogenation of bis-oxime (Vb), typically under standard conditions using hydrogen and a palladium/charcoal catalyst in methanol, delivers the desired 2-methoxymethyl-p-phenylenediamine (I). Alternatively, the precursor for the hydrogenation may be as well a diimine derivative (Va), such as 2-(methoxymethyl)cyclohexa-2,5-diene-1,4-dione hydrazine as described above.

The hydrogenation step is principally carried out in the presence of a hydrogen source. The hydrogen source may be selected, for example, from hydrazine or $H_2$. Typically, the hydrogenation may be carried out in the presence of a catalyst, for example a metal catalyst. Metal catalysts may be selected, for example, from the group consisting of Fe, Pd/C, Pd/(OH)$_2$, Raney-Ni, Pt/C, PtO$_2$ and mixtures thereof. In particular, the hydrogen source may be $H_2$, and the metal catalyst may be a Pd/C catalyst. The solvent(s) used in this step may be selected from the group consisting of 1,2-dimethoxyethane, pentane, cyclopentane, hexane, cyclohexane, benzene, toluene, methylacetate, ethylacetate, n-propylacetate, iso-propylacetate, n-butylacetate, methylpropionate, ethylpropionate, n-propylpropionate, iso-propylpropionate, n-butylpropionate, 1,4-dioxane, diethyl ether, tetrahydrofuran, methyl-tetrahydrofuran, n-butanol, isopropanol, n-propanol, ethanol, methanol, water and mixtures thereof. Preferably, the solvent may selected from the group consisting of methanol, ethanol, ethylacetate, toluene and mixtures thereof. From an ecological viewpoint, the solvent may preferably be selected from methanol, ethanol and/or ethylacetate, or an aqueous solution of methanol and/or ethanol. When using an aqueous solution, the water content is low enough to ensure complete solubilization of any diimine derivative (Va) and/or bis-oxime (Vb) present. In particular, the water content is below 50 wt %.

B1 Synthesis of 2-methoxymethyl-1,4-benzochinone (IV) Using 1,4-benzoquinone (VIII) as Starting Material

Reaction Scheme 2

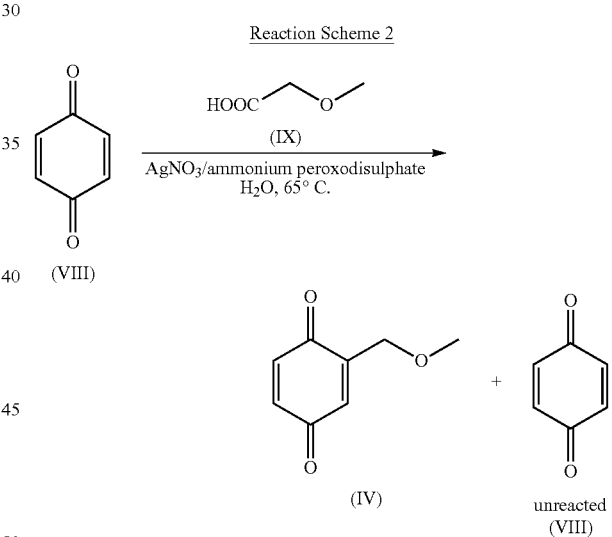

1,4-benzoquinone (VIII) is dissolved in a 1:1 water/methylenchloride solution and treated with silver nitrate. Radical alkylation of 1,4-benzoquinone (VIII) will commence by time controlled addition of ammonium peroxodisulphate as radical former and 2-methoxyacetic acid (IX). The reaction is complete after 1-2 h at medium temperature of max. 35°–38° C., limited by the boing point of methylenchloride. The refluxing methylenchloride will flush down any sublimed 1,4-benzoquinone (VIII) from the cooling device. Time controlled addition remains important as the decarboylylation of 2-methoxyacetic acid (IX) is sensitive to any access of the radical starter to react with 1,4-benzoquinone (VIII). The transformation rate is between 50-60%, hence unreacted 1,4-benzoquinone (VHF) is still present in the reaction mixture, beside some detectable di-alkylated byproducts (max. 1-2%). The aqueous mixture is treated with excess of methylene chloride to separate all inorganic matters from the organic phase.

Optionally, the above reaction may be carried out using an aqueous solution in the absence methylene chloride. Without methylene chloride, the yield will decrease for the conversion, since sublimed 1,4-benzoquinone (VIII) cannot be flushed down from the cooling device by the refluxing methylene chloride.

The solution is dried with sodium or magnesium sulphate, filtered and the solvent evaporated. The obtained crude product mixture has been observed to be light sensitive, hence the reaction course is preferable conducted in the dark. The residue is treated with water followed by standard steam distillation to completely remove all remaining 1,4-benzoquinone (VIII). This compound is known to form an azeotrope mixture with water and can be easily removed from the reaction mixture. After completion of the water steam distillation, the aqueous phase is extracted with methylenchloride, dried over sodium or magnesium sulphate, filtered and the solvent evaporated. Alternatively the crude reaction mixture can be distilled via thin film or short path evaporation under mild vacuum conditions to extract the water steam sensitive 1,4-benzoquinone (VIII) quantitatively from the reaction mixture. 2-Methoxymethyl-1,4-benzochinone (IV) is observed to be very sensitive to light. Accordingly, this compound advantageously is handled in the dark, and any reactions involving this compound are carried out in the dark.

B2 Synthesis of 2-Methoxymethyl-1,4-benzochinone (IV) Using 2-methyl-1,4-benzochinone (II) as Starting Material Reaction Scheme 3

(II)

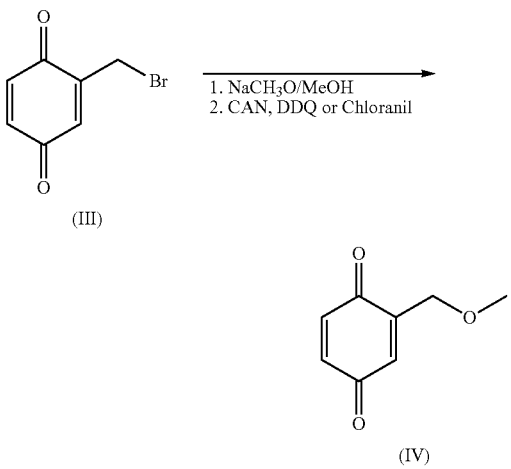

Bromination of 2-methyl-1,4-benzochinone (II) is carried out with N-Bromo-succinimide (NBS) in carbon tetrachloride using azo-iso-butyronitril (AIBN) as radical starter. The mixture is being refluxed for 2-4 h, leading to 2-bromomethyl-1,4-benzochinone (II). After the solvent is distilled off in vacuum, the reaction mixture is treated with sodium methylate in methanol to form subsequently the corresponding ether (IV). 2-Methoxymethyl-1,4-benzochinone (IV) is observed to be very sensitive to light. Accordingly, this compound advantageously is handled in the dark, and any reactions involving this compound are carried out in the dark. If partial re-aromatization is observed, the reaction mixture can be re-oxidized (using Ceric ammonium nitrate (CAN), dichloro-dicyano-benzochinone DDQ or Chloranil), to obtain 2-methoxymethyl-1,4-benzochinone (IV) with optimized yield. This intermediate can be purified via recrystallization as needed.

B3 Synthesis of 2-methoxymethyl-1,4-benzochinone (IV) Using 1,4-dimethoxy-2-methyl-benzene (VI) as Starting Material Reaction Scheme 4

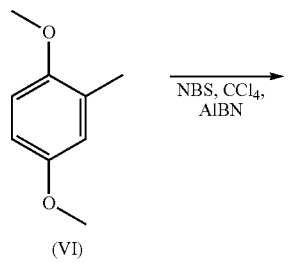

(VI)

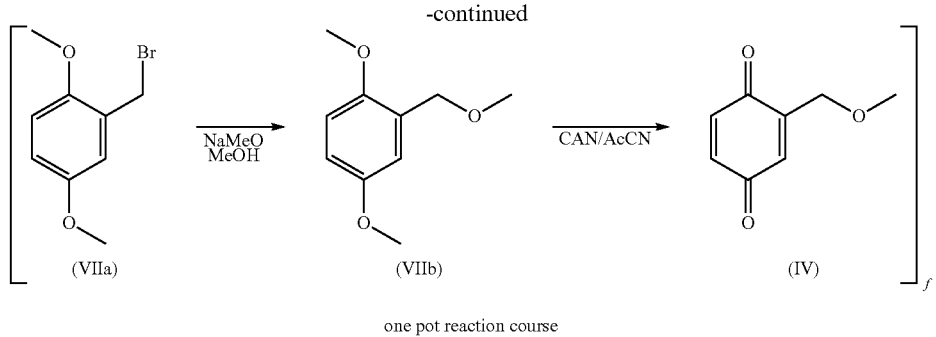

one pot reaction course

Bromination of 1,4-dimethoxy-2-methyl-benzene (VI) is carried out with N-Bromo-succinimide (NBS) in carbon tetrachloride using azo-iso-butyronitril (AIBN) as radical starter. The mixture is being refluxed for 2-4 h, to produce the bromo derivative (VIIa) which is not isolated. The latter is treated with water and the organic phase is separated to also filter off the succinimide. The solvent is distilled off in vacuum immediately and the reaction mixture is treated with sodium methylate in methanol, heated for 1-3 h to reflux to form subsequently the corresponding 1,4-dimethoxy-2-(methoxymethyl)benzene (VIIb). The mixture is filtered and the methanol removed. The resulting residue is dissolved in acetonitrile and oxidized to obtain 2-methoxymethyl-1,4-benzochinone (IV). Oxidizers can be selected from the group consisting of CAN (ceric ammonium nitrate), dichloro-dicyano-benzochinone DDQ, Chloranil, hydrogen peroxide in hydrochloric medium of hydrogen peroxide, typically in the presence of a catalyst, for example metal complexes as catalyst such as titanium superoxide, oxoperoxo molybdenum(VI) or tungsten(VI) complexes.

As noted above, 2-methoxymethyl-1,4-benzochinone (IV) is observed to be very sensitive to light. Accordingly, this compound advantageously is handled in the dark, and any reactions involving this compound are carried out in the dark.

The solvent(s) used in this synthesis may be selected from the group consisting of 1,2-dimethoxyethane, ethyl acetate, pentane, cyclopentane, hexane, cyclohexane, benzene, toluene, 1,4-dioxane, diethyl ether, tetrahydrofuran, methyl-tetrahydrofuran, n-pentanol, n-butanol, acetic acid, propionic acid, oxalic acid, malonic acid, sulphuric acid, phosphoric acid, iso-pentanol, t-butanol, isopropanol, n-propanol, ethanol, methanol, glycols, hydrogen chloride, water and mixtures thereof. Seen from an ecological viewpoint, the solvents used in this synthesis are selected from the group consisting of n-butanol, isopropanol, n-propanol, ethanol and/or methanol, and aqueous solutions thereof.

B4 Synthesis of
2-methoxymethyl-1,4-benzochinone (IV) Using
3-(hydroxymethyl)phenol (XIX) as Starting
Material Reaction Scheme 5

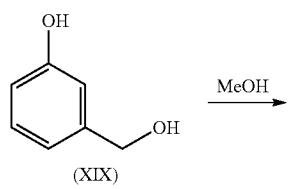

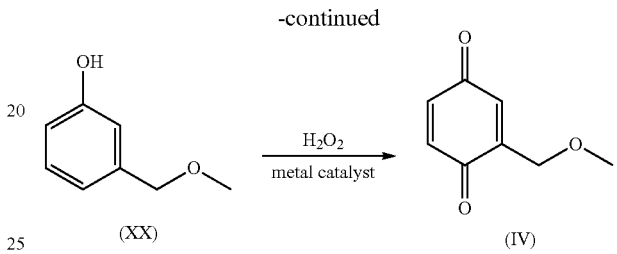

Methylation of 3-(hydroxymethyl)phenol (XIX) (alternatively also with (3-methoxyphenyl)methanol) in methanol yields 3-(methoxymethyl)phenol (XX). 3-(Hydroxymethyl)phenol (XIX) is dissolved in methanol while an excess of dimethylsulphate is added and the mixture is stirred at reflux for 1-6 h. The methylation agent may be selected from the group consisting of dimethylsulphate, chloromethane, bromomethane, methyl iodide, dimethyl sulfate and mixtures thereof. Preferable, the methylation agent is dimethyl sulfate.

The methylation may be carried out using at least one phase transfer catalyst. The phase transfer catalyst(s) may be selected from the group consisting of benzyl trialkyl ammonium salts, alternatively from the group consisting of chloride, bromide or sulfate salts of benzyl trimethyl ammonium, benzyl triethyl ammonium, benzyl tripropyl ammonium, benzyl tributyl ammonium and mixtures thereof. Preferably, the phase transfer catalyst is benzyl tributyl ammonium chloride.

The solvent(s) used for the methylation may be selected from the group consisting of 1,2-dimethoxyethane, pentane, cyclopentane, hexane, cyclohexane, benzene, toluene, 1,4-dioxane, diethyl ether, tetrahydrofuran, methyl-tetrahydrofuran, n-pentanol, iso-pentanol, t-butanol, isopropanol, n-propanol, ethanol, methanol, water, glycols and mixtures thereof. Preferably, the solvent(s) are selected from the group consisting of alcohols, in particular the above alcohols, mixtures thereof and aqueous solutions thereof.

Such a synthesis route has been already described in the literature, e.g. in the Journal of Molecular Catalysis A: Chemical, 273(1-2), 118-132; 2007 using sodium methylate as a methoxylating agent in the presence of methanol.

As a next step, 3-(methoxymethyl)phenol (XX) needs to be oxidized to obtain the chinone intermediate 2-methoxymethyl-1,4-benzochinone (IV) using metal catalysts (e.g. titanium superoxide or tungsten/molebdenum complexes) and hydrogen peroxide.

Oxidation can also be carried out in solvents selected from the group of 1,2-dimethoxyethane, pentane, cyclopentane, acetone, ethyl acetate, methyl acetate, chloroform, methylene chloride, acetonitrile, hexane, cyclohexane, benzene, toluene, 1,4-dioxane, diethyl ether, tetrahydrofuran, methyl-tetrahydrofuran, n-pentanol, n-butanol, acetic acid, propionic acid, oxalic acid, malonic acid, sulphuric acid, phosphoric acid, iso-pentanol, t-butanol, isopropanol, n-propanol, ethanol, methanol, glycols, hydrogen chloride, water and mixtures thereof. Preferably, the solvent(s) are selected from the group consisting of n-butanol, isopropanol, n-propanol, ethanol and methanol, and aqueous solutions thereof.

Oxidizers can be selected of the group of CAN (ceric ammonium nitrate), dichloro-dicyano-benzochinone DDQ, Chloranil, hydrogen peroxide in hydrochloric medium of hydrogen peroxide in the presence of metal complexes as catalyst such as titanium superoxide, oxoperoxo molybdenum(VI) or tungsten(VI) complexes.

Acids used herein can be selected from the group of at least one mineral or organic acid. The mineral or organic acid may be selected from the group consisting of hydrogen chloride, trifluoroacetic acid, sulfuric acid, sulfurous acid, carbonic acid, nitric acid, acetic acid, propionic acid, phosphoric acid and mixtures thereof. Preferred mineral or organic acids are hydrogen chloride, sulfuric acid, sulfurous acid, acetic acid and mixtures thereof. In particular, the mineral or organic acid may be acetic acid.

Purification may be carried out via recrystallization to eliminate traces of impurities still present. Solvents for the recrystallization may be selected from the group of 1,2-dimethoxyethane, ethyl acetate, pentane, cyclopentane, hexane, cyclohexane, benzene, toluene, 1,4-dioxane, diethyl ether, tetrahydrofuran, methyl-tetrahydrofuran, n-pentanol, n-butanol, acetic acid, propionic acid, oxalic acid, malonic acid, sulphuric acid, phosphoric acid, iso-pentanol, t-butanol, isopropanol, n-propanol, ethanol, methanol, glycols, hydrogen chloride, water and mixtures thereof. Preferred solvents are n-butanol, isopropanol, n-propanol, ethanol, methanol, acetic acid, propionic acid, oxalic acid, malonic acid, hydrogen chloride, sulphuric acid, phosphoric acid and mixtures thereof, in particular n-propanol, acetic acid, propionic acid, oxalic acid, malonic acid, hydrogen chloride, sulphuric acid, phosphoric acid and mixtures thereof.

C Synthesis of 2-Methoxymethyl-p-phenylenediamine (I) Using 1,4-benzoquinone (VIII) as Starting Material, with p-phenylenediamine (XI) as a By-Product

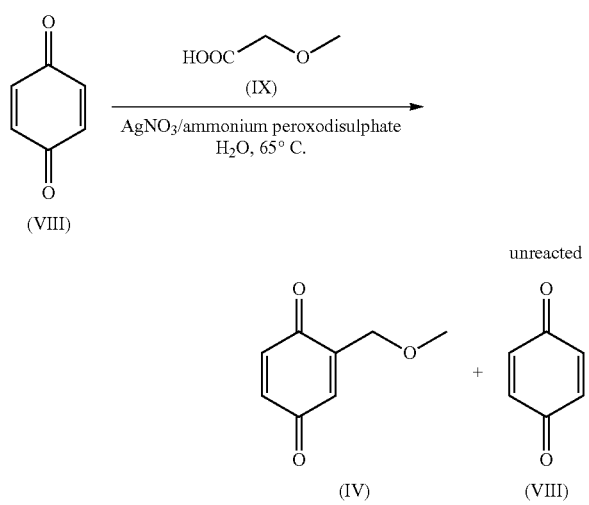

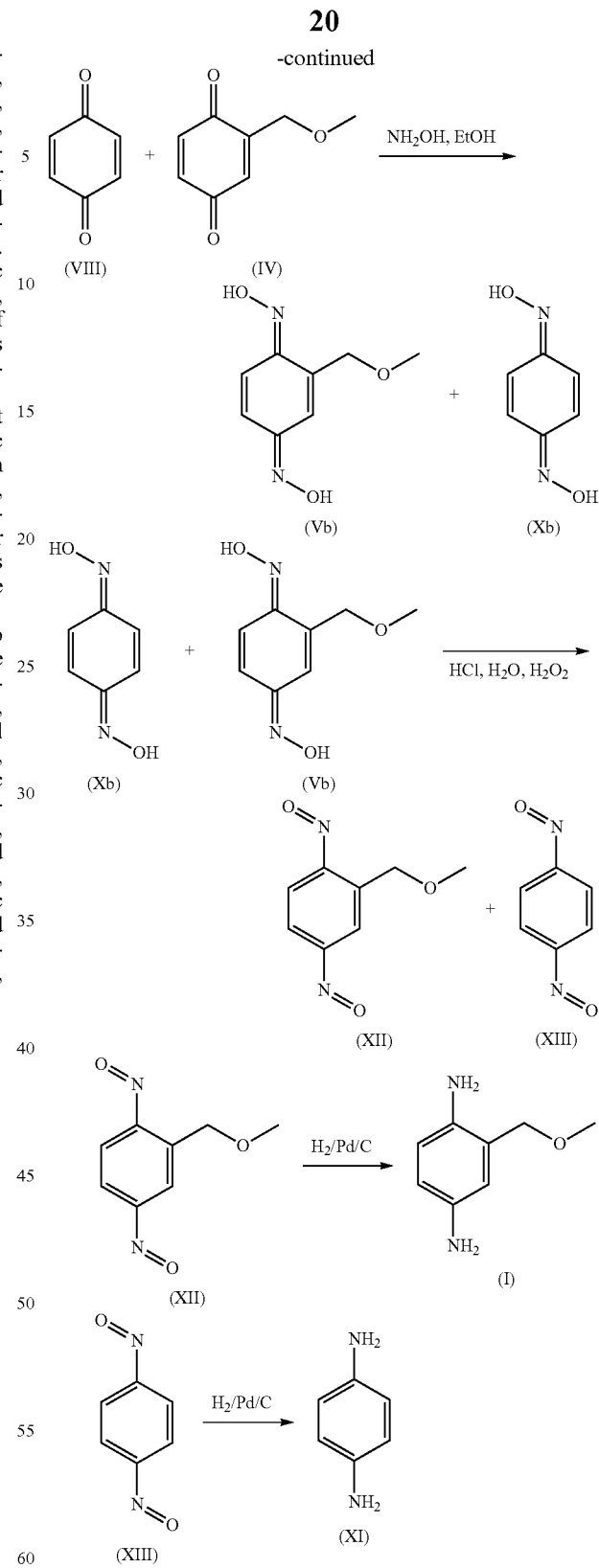

1,4-benzoquinone (VIII) is dissolved in water and treated with silver nitrate and 2-methoxyacetic acid (IX). Radical alkylation of 1,4-benzoquinone (VIII) will commence by time controlled addition of ammonium peroxodisulphate as radical former. The reaction is complete after 1-2 h at medium temperature. Time controlled addition remains important as the decarboylylation of 2-methoxyacetic acid (IX) is sensitive to any access of the radical starter to react with 1,4-benzoquinone (VIII). The transformation rate is between 40 and 50%, hence unreacted 1,4-benzoquinone (VIII) is still present in the reaction mixture, beside some detectable di-alkylated byproducts. The aqueous mixture is treated with methylene chloride to separate all inorganic latters from the organic phase. The solution is dried with sodium or magnesium sulphate, filtered and the solvent evaporated. At that stage, no separation can be run as only a small scale column chromatography is suitable to separate the different chinone compounds. The obtained product mixture has been observed to be light sensitive, hence the reaction course is preferable conducted in the dark.

The product residue is subsequently dissolved in ethanol, heated to reflux in the presence of a base, preferably sodium acetate or calcium carbonate, and in the presence of an amine source NH2-R1 to form the corresponding diimines 2-(methoxymethyl)-N1(R1),N4(R1)-cyclohexa-2,5-diene-1,4-diimine (Va) and N1(R1),N4(R1)-cyclohexa-2,5-diene-1,4-diimine (Xa). Moiety R1 of the amine source NH2-R1 is selected from OH, NH2, linear or branched (C1-C6)alkyl which optionally may be substituted with OH, linear or branched (C1-C6)alkylene-(C5-C6)cycloalkyl and linear or branched (C1-C6)alkylbenzol. Hydroxylamine, hydrazine (hydrate) and the (C1-C6)alkylamines are preferably used as the amine source, with hydroxylamine being most preferred, followed by hydrazine (hydrate).

When refluxing the dissolved product residue in the presence of the base with 3 equivalents hydroxylamine, the corresponding bis-oximes 2-(methoxymethyl)-cyclohexa-2,5-diene-1,4-dione oxime (Vb) and cyclohexa-2,5-diene-1,4-dione oxime (Xb) are obtained. The base may be selected from sodium acetate, calcium carbonate, sodium carbonate, potassium carbonate, DBU, DBN, Huenig Base, ammonium sulphate, sodium hydrogencarbonate or potassium hydrogencarbonate, preferably sodium acetate or calcium carbonate.

After the conversion to the diimine derivatives or bis-oxime derivatives, respectively, is completed, the intermediate products are filtered and the solvent is removed in vacuum.

The diimine derivatives (Va) and (Xa) or the bis-oxime compounds (Vb) and (Xb), respectively, are converted into the tautomeric bis-nitroso compounds (XII) and (XIII) via smooth oxidation in hydrochloric acid with hydrogen peroxide. An aqueous solution of the product residue from step (b1) is prepared and treated with 30% hydrochloric acid. Slow addition of hydrogen peroxide initiates the oxidation to form the nitroso derivatives (XII) and (XIII). These compounds are bright yellow-greenish and show a very good tendency for crystallization. This effect can be positively used to separate the target compound 2-(methoxymethyl)-1,4-dinitroso-benzene (XII) from other bis-nitroso by-products due to their sufficiently different melting and boing point.

Elimination of further byproducts and subsequent separation of compound (XIII) from the reaction mixture is executed via recrystallization in various solvents or vacuum distillation.

Solvents for the recrystallization may be selected from the group of 1,2-dimethoxyethane, pentane, ethyl acetate, cyclopentane, hexane, cyclohexane, benzene, toluene, 1,4-dioxane, diethyl ether, tetrahydrofuran, methyl-tetrahydrofuran, n-pentanol, n-butanol, acetic acid, propionic acid, oxalic acid, malonic acid, sulphuric acid, phosphoric acid, iso-pentanol, t-butanol, isopropanol, n-propanol, ethanol, methanol, glycols, hydrogen chloride, water and mixtures thereof. Preferably, the solvent is selected from the group consisting of n-butanol, isopropanol, n-propanol, ethanol, methanol, acetic acid, propionic acid, oxalic acid, malonic acid, hydrogen chloride, sulphuric acid, phosphoric acid and mixtures thereof. In particular, the solvent may be selected from the group consisting of n-propanol, acetic acid, propionic acid, oxalic acid, malonic acid, hydrogen chloride, sulphuric acid, phosphoric acid and mixtures thereof.

Final hydrogenation delivers the desired 2-methoxymethyl-p-phenylenediamine (I), and, from the same reaction course, once the bi-nitroso starters have been separated, the commercially interesting p-phenylene-diamine (XI) in comparable yields.

This step is principally carried out in the presence of a hydrogen source. The hydrogen source may be selected from hydrazine or $H_2$, for example. The hydrogenation typically is carried out in the presence of a catalyst, for example a metal catalyst such as a metal catalyst selected from the group consisting of Fe, Pd/C, Pd/(OH)$_2$, Raney-Ni, Pt/C, PtO$_2$ and mixtures thereof. In particular, the hydrogen source may be $H_2$ with a Pd/C catalyst. The solvent(s) used in this step may be selected from the group consisting of 1,2-dimethoxyethane, pentane, cyclopentane, hexane, cyclohexane, benzene, toluene, methylacetate, ethylacetate, n-propylacetate, iso-propylacetate, n-butylacetate, methylpropionate, ethylpropionate, n-propylpropionate, iso-propylpropionate, n-butylpropionate, 1,4-dioxane, diethyl ether, tetrahydrofuran, methyl-tetrahydrofuran, n-butanol, isopropanol, n-propanol, ethanol, methanol, water and mixtures thereof. Preferably, the solvent may selected from the group consisting of methanol, ethanol, water, ethylacetate, toluene and mixtures thereof. From an ecological viewpoint, the solvent may preferably be selected from methanol, ethanol and/or ethylacetate, or an aqueous solution thereof.

D Synthesis of 2-methoxymethyl-p-phenylenediamine (I) Using p-hydrochinone (XIV) as Starting Material Reaction Scheme 7

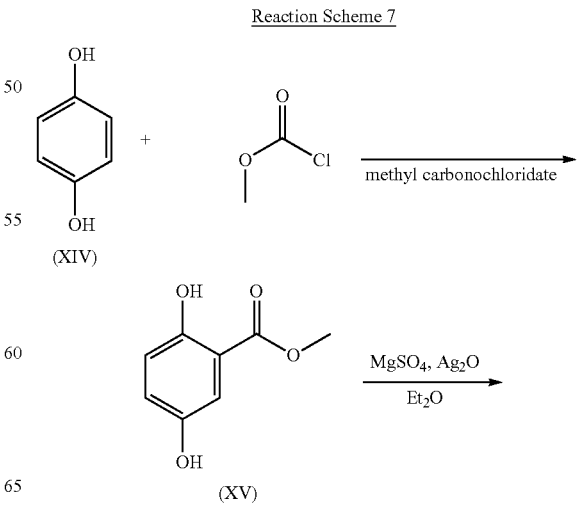

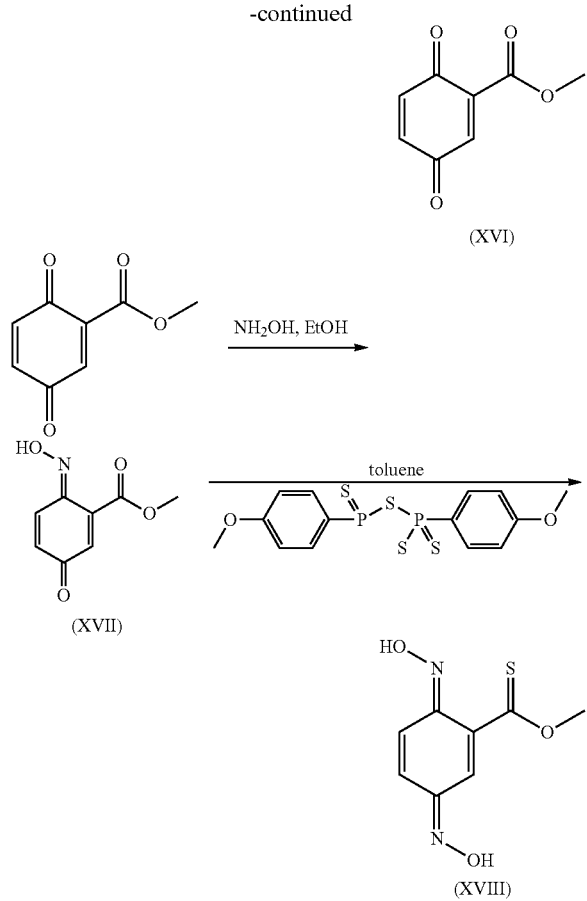

This process starts with a classic Friedel Crafts acylation. Therefore, acylation of p-hydrochinone (XV) is carried out with methyl-chlorformiate in the presence of a Lewis acid as catalyst in dichloro methane. Other preferred solvents are also chloroform, of 1,2-dimethoxyethane, pentane, cyclopentane, hexane, cyclohexane, benzene, toluene, methylacetate, ethylacetate, n-propylacetate, iso-propylacetate, n-butylacetate, methylpropionate, ethylpropionate, n-propylpropionate, iso-propylpropionate, n-butylpropionate, 1,4-dioxane, diethyl ether, tetrahydrofuran, methyl-tetrahydrofuran, n-butanol, isopropanol, n-propanol, ethanol, methanol, alternatively from the group consisting of methanol, ethylacetate, toluene and mixtures thereof.

The Lewis acid is selected from the group of aluminium chloride, indium chloride, zinc oxide, zinc chloride, iron chloride, iron sulphate and ytterbium triflate.

The reaction mixture is filtered and the solvent removed in vacuum. The obtained solid can be recrystallized in solvents from the group of, 2-dimethoxyethane, pentane, cyclopentane, acetone, ethyl acetate, methyl acetate, chloroform, methylene chloride, hexane, cyclohexane, benzene, toluene, 1,4-dioxane, diethyl ether, tetrahydrofuran, methyl-tetrahydrofuran, n-pentanol, n-butanol, acetic acid, propionic acid, oxalic acid, malonic acid, sulphuric acid, phosphoric acid, iso-pentanol, t-butanol, isopropanol, n-propanol, ethanol, methanol, glycols, hydrogen chloride, water and mixtures thereof, alternatively from the group consisting of n-butanol, isopropanol, n-propanol, ethanol, methanol, acetic acid, propionic acid, oxalic acid, malonic acid, hydrogen chloride, sulphuric acid, phosphoric acid and mixtures thereof, alternatively from the group consisting of n-propanol, acetic acid, propionic acid, oxalic acid, malonic acid, hydrogen chloride, sulphuric acid, phosphoric acid and mixtures thereof. The so obtained intermediate methyl 2,5-dihydroxybenzoate (XV) is then oxidized to form the chinone intermediate methyl 3,6-dioxocyclohexa-1,4-diene-1-carboxylate (XVI). Compound (XV) is dissolved in diethyl ether, followed by addition of magnesium sulphate, silver oxide and hydrogen peroxide. Once oxidation is complete (the solution turns colored while forming the chinone derivative), the latter is filtered off, the solvent removed under vacuum and immediately used in the next step.

Oxidation can also be carried out in solvents selected from the group of 1,2-dimethoxyethane, pentane, cyclopentane, acetone, ethyl acetate, methyl acetate, chloroform, methylene chloride, acetonitrile, hexane, cyclohexane, benzene, toluene, 1,4-dioxane, diethyl ether, tetrahydrofuran, methyl-tetrahydrofuran, n-pentanol, n-butanol, acetic acid, propionic acid, oxalic acid, malonic acid, sulphuric acid, phosphoric acid, iso-pentanol, t-butanol, isopropanol, n-propanol, ethanol, methanol, glycols, hydrogen chloride, water and mixtures thereof, alternatively from the group consisting of n-butanol, isopropanol, n-propanol, ethanol and methanol. Oxidizers can be selected of the group of CAN (ceric ammonium nitrate), dichloro-dicyano-benzochinone DDQ, Chloranil, hydrogen peroxide in hydrochloric medium of hydrogen peroxide. The oxidation may be carried out in the presence of a catalyst, for example metal complexes as catalyst, such as titanium superoxide, oxoperoxo molybdenum(VI) or tungsten(VI) complexes.

The chinone intermediate methyl 3,6-dioxocyclohexa-1,4-diene-1-carboxylate (XVI) is reacted with 3 equivalents of hydroxylamine in ethanol in the presence of a base to form the corresponding bis-oxime (3Z,6E)-3,6-bis(hydroxyimino)cyclohexa-1,4-diene-1-carboxylic acid (XVII). The base may be selected from calcium carbonate, sodium acetate, sodium carbonate, potassium carbonate, DBU, DBN, Huenig Base, ammonium sulphate, sodium hydrogencarbonate or potassium hydrogencarbonate.

In preparation to reduce the ester, transformation of (XVII) into the corresponding thionoester O-methyl (3Z,6E)-3,6-bis(hydroxyimino)cyclohexa-1,4-diene-1-carbothioate (XVIII) via $P_4O_{10}$ or Lawsson's reagent in toluene is required. The thionating agent can be easily prepared according to literature procedures in situ from $P_2O_5$ and anisole. Thionation of the esterbis-oxime (3Z,6E)-3,6-bis(hydroxyimino)cyclohexa-1,4-diene-1-carboxylic acid (XVII) required 2-4 h reflux in organic solvents. The solvent(s) used in this step may be selected from the group consisting of 1,2-dimethoxyethane, pentane, cyclopentane, acetone, ethyl acetate, methyl acetate, chloroform, methylene chloride, hexane, cyclohexane, benzene, toluene, 1,4-dioxane, diethyl ether, tetrahydrofuran, methyl-tetrahydrofuran, n-pentanol, n-butanol, acetic acid, propionic acid, oxalic acid, malonic acid, sulphuric acid, phosphoric acid, iso-pentanol, t-butanol, isopropanol, n-propanol, ethanol, methanol, glycols, hydrogen chloride. Preferably, the solvent may be selected from the group consisting of n-butanol, isopropanol, n-propanol, ethanol and methanol. From an ecological viewpoint, the solvent may preferably be selected from methanol, ethanol and/or ethylacetate, or an aqueous solution thereof.

Final hydrogenation delivers the desired 2-methoxymethyl-p-phenylenediamine (I). This step is principally carried out in the presence of a hydrogen source. The hydrogen source may be selected from hydrazine or $H_2$. Typically, the hydrogenation may be carried out in the presence of a catalyst, for example a metal catalyst such as a metal catalyst selected from the group consisting of Fe, Pd/C, Pd/(OH)$_2$, Raney-Ni, Pt/C, PtO$_2$ and mixtures thereof. In particular, the hydrogen source may be H$_2$ with a Pd/C catalyst. The solvent(s) used in this step may be selected from the group consisting of 1,2-dimethoxyethane, pentane, cyclopentane, hexane, cyclohexane, benzene, toluene, methylacetate, ethylacetate, n-propylacetate, iso-propylacetate, n-butylacetate, methylpropionate, ethylpropionate, n-propylpropionate, iso-propylpropionate, n-butylpropionate, 1,4-dioxane, diethyl ether, tetrahydrofuran, methyl-tetrahydrofuran, n-butanol, isopropanol, n-propanol, ethanol, methanol, water and mixtures thereof. Preferably, the solvent may selected from the group consisting of methanol, ethanol, water, ethylacetate, toluene and mixtures thereof. From an ecological viewpoint, the solvent may preferably be selected from methanol, ethanol and/or ethylacetate, or an aqueous solution thereof.

The dimensions and values disclosed herein are not to be understood as being strictly limited to the exact numerical values recited. Instead, unless otherwise specified, each such dimension is intended to mean both the recited value and a functionally equivalent range surrounding that value. For example, a concentration disclosed as "1%" is intended to mean "about 1%." Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention;

EXAMPLES

The following non-limiting examples further illustrate the present invention. The examples are given solely for the purpose of illustration and are not to be construed as limitations of the present invention, as many variations thereof are possible without departing from the spirit and scope of the invention, which would be recognized by one of ordinary skill in the art. All concentrations are listed as weight percent, unless otherwise specified.

Example 1: Synthesis of 2-methoxymethyl-p-phenylenediamine (I) Using 1,4-benzoquinone (VIII) as Starting Material (1) Synthesis of 2-methoxymethyl-1,4-benzochinone (IV)

A three necked flask was fitted with a reflux condenser and a thermometer and is charged with 1 eq.=3 g (27.5 mmol) 1,4-benzoquinone (VIII), 1.5 eq=3.71 g (41.2 mmol) 2-methoxyacetic acid (IX) in the presence of 0.3 eq.=1.41 g (8.24 mmol) silver nitrate and a 1:1 mixture of methylenechloride and water (98 mL). The 2-phase mixture was stirred until complete dissolution was observed. The mixture is then heated to 40° C. at reflux to float back any sublimated 1,4-benzoquinone (VIII) on the top of the flask. Then a solution of ammonium peroxodisulphate as radical former, 1.05 eq=6.72 g (28.8 mmol) in water was slowly, time-controlled, added at a rate of 10 mL/h using a syringe driver or a pump (dosimat). Throughout addition, the reaction mixture is maintained at 40° C. After the addition is completed, the mixture is stirred for further 15 min. at 40° C. TLC and HPLC analysis shows a 60% conversion rate from the benzochinone (VIII) to the desired intermediate 2-methoxymethyl-1,4-benzochinone (IV). After cooling to room temperature, another portion of methylene chloride was added (130 mL). The formed layers were separated and the aqueous layer was extracted again 3 times with methylene chloride (100 ml each). The combined organic layers were dried over Na$_2$SO$_4$, filtered and concentrated under reduced pressure at room temperature in the dark. The recovery of the silver can be done by wet chemical methods. The following wet chemistry method illustrates how silver can be recovered: the aqueous phase is treated with caustic soda according to the following scheme:

$$2AgNO_3 + 2NaOH \rightarrow Ag_2O + 2NaNO_3 + H_2O$$

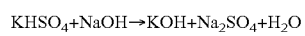
$$KHSO_4 + NaOH \rightarrow KOH + Na_2SO_4 + H_2O$$

Potassium hydrogen sulphate as the typical end product of reacted peroxodisulfate is converted in alkaline medium to alkalimetal sulphate salt while the remaining silvernitrate is precipitated as silveroxide. The collected residue via filtration is treated with stoichiometrically amounts of nitric acid to form again a neutral solution of silvernitrate:

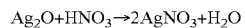
$$Ag_2O + HNO_3 \rightarrow 2AgNO_3 + H_2O$$

(2) Removal of Unreacted 1,4-benzoquinone (VIII)

The residue is placed in a flask and prepared for a short path destillation and treated with 100 ml water. The aqueous suspension is gently heated to 30° C. to allow controlled sublimation of 1,4-benzoquinone (VIII) to be separated from the crude reaction mixture. This procedure is conducted for 24 h where a significant amount of 1,4-benzoquinone (VIII) could be already collected on the cooling device. Then the mixture is heated to 40° C. under mild vacuum (ca. 200-300 mbar) to completely evaporate the water volatile 1,4-benzoquinone (VIII) and collect it on the cooling device. This process allows to recollect the unreacted 1,4-benzoquinone (VIII) and recycle the material for the next campaign. The water of the remaining aqueous suspension which is formed after the destillation process is then removed while applying a stronger vacuum. The crude product 2-methoxymethyl-1,4-benzochinone (IV) will be subsequently converted in the next step without further purification and isolation.

In lab scale, the residue from above may be purified by column chromatography on silica gel with pentane/methylene chloride, diethyl ether to obtain 2-methoxymethyl-1,4-benzochinone (IV) as an orange solid.

(3) Conversion to 2-(methoxymethyl)-cyclohexa-2,5-diene-1,4-dione oxime (Vb)

A three necked flask is charged with 1.50 g (15.00 mmol) calcium carbonate and 2 g (13.15 mmol based on 2-methoxymethyl-1,4-benzochinone) crude mixture obtained after the short path distillation from step (2). This mixture contains 2-methoxymethyl-1,4-benzochinone (IV) and some dialkylated species <2%. The mixture was dissolved in 50 mL Ethanol. After addition of 1.08 g hydroxylamine (32.88 mmol), the mixture is heated to reflux for 12 h until all starting materials are consumed (qualitatively by TLC). The mixture is filtered hot and the ethanol removed under reduced pressure. The obtained crude material is purified by recrystallization and then subsequently used as starting material in the next step c). The recrystallization is done in solvents such as hexane, methyl-hexane, ethanol, methanol, n-propanol, iso-propanol or petrolether. Therefore the crude obtained from this step is dissolved in the respective solvent and heated slowly to reflux. Gentle cooling precipitates 2.23 g (12.23 mmol) 2-(methoxymethyl)-cyclohexa-2,5-diene-1,4-dione oxime (Vb) from the solution in 93% yield. The residue is collected via vacuum filtration and washed with cold petrolether and dried in vacuum.

(4) Hydrogenation to 2-methoxymethyl-p-phenylenediamine (I)

0.60 g (3.29 mmol) 2-(methoxymethyl)-cyclohexa-2,5-diene-1,4-dione oxime (Vb) and water moistured catalyst Pd/C 10% (5% by weight) showing a water content of about 50% by weight are suspended in ethanol (ca. 8 parts by volume). If an aqueous suspension of the catalyst exhibits an acidic pH-value, it should be treated with a base in advance and filtrated before use. Ethylacetate or methanol alternatively might be used as solvent. The composition is transferred under an inert atmosphere into a pressure vessel which has been evacuated and flooded with nitrogen. For safety reasons the vessel is again evacuated and flooded with nitrogen and finally charged with hydrogen up to a pressure of approx. 2 bar absolute. The hydrogenation starts in the presence of hydrogen after switching on the stirrer. At the same time the cooling of the reaction mixture is started. The cooling is controlled in such a way, that the reaction temperature is kept at approx. 20° C. At room temperature the take-up of hydrogen is moderate. The end of the hydrogen consumption appears from falling reaction temperature and decreasing take-up of hydrogen. To complete the conversion the reaction mixture is stirred further at room temperature for an additional period of 30 min. Then the reaction mixture is filtered under an inert atmosphere (it is important to have the reaction temperature at room temperature to avoid the crystallization of the 2-methoxymethyl-p-phenylenediamine, with may occur at lower temperature). The catalyst residue is washed twice with ethaylacetate or methanol (1 part by volume). After cooling the crude product precipitates. Further recrystallization from toluene yields 0.45 g (2.90 mmol) pure 2-methoxymethyl-p-phenylenediamine (I). The yield, based on the crude 2-methoxymethyl-1,4-benzochinone (IV) reaction mixture, is 88.8% of theoretical. The actual yield accordingly should be higher than 90.0%.

Example 2 Synthesis of 2-methoxymethyl-p-phenylenediamine (I) Using 1,4-benzoquinone (VIII) as starting material (1) Synthesis of 2-methoxymethyl-1,4-benzochinone (IV)

A three necked flask was fitted with a reflux condenser and a thermometer and is charged with 462 g 1,4-benzoquinone (VIII), 1.5 eq=578 g 2-methoxyacetic acid (IX) in the presence of 0.05 eq.=36.31 g silver nitrate and a 1:1 mixture of dichloromethane and water (4620 mL each). The 2-phase mixture was stirred until complete dissolution was observed. The mixture is then heated to 39° C. at reflux to float back any sublimated 1,4-benzoquinone (VIII) on the top of the flask. Then a solution of 1073 g ammonium peroxodisulphate as radical former in 2080 mL water was slowly added within 1 h. Throughout addition, the reaction mixture is maintained at 40° C. After the addition is completed, the mixture is stirred for further 2 h at reflux at 39° C. HPLC analysis shows a 60% coversion rate from the benzochinone (VIII) to the desired intermediate 2-methoxymethyl-1,4-benzochinone (IV). After cooling to room temperature, the latter was filtered off using a pressure filter. The formed layers were separated and the aqueous layer (ca. 6 L) was extracted again 2 times with dichloromethane (960 ml each). The combined organic layers were dried over $Na_2SO_4$, filtered and concentrated under reduced pressure at room temperature in the dark for 1.5 h to yield 770 g of crude brown oil. Silver recovery can be done as disclosed in example 1. The HPLC profile is as follows:

| Wavelength | 254 nm | 234 nm |
|---|---|---|
| 1,4-benzoquinone (VIII) | 35.02 area % | 38.11 area % |
| 2-methoxymethyl-1,4-benzochinone (IV) | 60.94 area % | 59.00 area % |
| Dialkylated byproducts | 3.96 area % | 2.90 area % |

(2) Removal of Unreacted 1,4-benzoquinone (VIII)

The crude oil (770 g) residue is placed in a flask while 10 parts by volume (7.7 L) deionized water are added. The water steam distillation is started while adjusting the vacuum to 80 mbar and maintaining the water bath at 45° C. to keep the steam temperature at max. 40° C. After 1 h yellow crystals begin to precipitate at the condenser. As no reflux was detected with these conditions, the water bath temperature and the vacuum were slowly adjusted over 90 minutes to 65° C. and to 55 mbar, respectively. The formation of yellow crystals strongly increases while reflux is maintained. After 3 h, the steam distillation is stopped while ca. 6 L water have been distilled. The brownish residue is treated once more with 2.3 L deionized water and a second steam distillation is started to further decrease the content of 1,4-benzoquinone (VIII). The water bath temperature is set to 70° C. and the vacuum is set to 50 mbar. Further precipitation of yellow crystals are observed. After 1 h the distillation was stopped as the reflux was observed to be colorless which indicated that no more 1,4-benzoquinone (VIII) is precipitated at the condenser.

The crude material is dissolved in dichloromethane, filtered and evaporated to show the following analysis by HPLC:

| Wavelength | 254 nm | 234 nm |
|---|---|---|
| 1,4-benzoquinone (VIII) | 1.82 area % | 2.98 area % |
| 2-methoxymethyl-1,4-benzochinone (IV) | 89.79 area % | 90.18 area % |
| Dialkylated byproducts | 8.16 area % | 6.25 area % |

10' This quality is sufficient to be passed on to the next reaction step (3) for the conversion into 2-(methoxymethyl)-cyclohexa-2,5-diene-1,4-dione oxime (Vb). Step (3), the conversion of 2-methoxymethyl-1,4-benzochinone (IV) into 2-(methoxymethyl)-cyclohexa-2,5-diene-1,4-dione oxime (Vb) and step (4), the subsequent hydrogenation of the 2-(methoxymethyl)-cyclohexa-2,5-diene-1,4-dione oxime (Vb) to yield the desired 2-methoxymethyl-p-phenylenediamine (I) can be processed as already disclosed in example 1.

However, the recovered 1,4-benzoquinone (VIII) is still contaminated with 2-methoxymethyl-1,4-benzochinone (IV) which has also been partially distilled in the water steam stream. The HPLC analysis of the recovered 1,4-benzoquinone (VIII) shows the following profile:

| Wavelength | 254 nm | 234 nm |
| --- | --- | --- |
| 1,4-benzoquinone (VIII) | 83.21 area % | 85.96 area % |
| 2-methoxymethyl-1,4-benzochinone (IV) | 16.80 area % | 14.04 area % |
| Dialkylated byproducts | 0.00 area % | 0.00 area % |

Due to the known extreme high volatility of 1,4-benzoquinone (VIII) at room temperature, the following simple procedure finally leads to a superior quality without applying a water steam distillation to further reduce process complexity. The crude material as isolated in step (1) of this example is treated with 10 parts by volume of deionized water. The mixture is stirred overnight for 16 h at room temperature in a closed vessel applying very gentle vacuum conditions (ca. 700-800 mbar). The 1,4-benzoquinone (VIII) is completely precipitated at the top roof of the vessel and could be isolated directly from there. The aqueous residue is treated with small portions of dichloromethane and the layers are separated. The organic phase is evaporated and the residue shows the following analytical composition by HPLC:

| Wavelength | 254 nm | 234 nm |
| --- | --- | --- |
| 1,4-benzoquinone (VIII) | 0.19 area % | 0.14 area % |
| 2-methoxymethyl-1,4-benzochinone (IV) | 98.8 area % | 98.00 area % |
| Dialkylated byproducts | 1.02 area % | 1.16 area % |

This demonstrates that very mild conditions (very gentle vacuum and room temperature) in aqueous medium is perfectly suitable to almost quantitatively remove the unreacted 1,4-benzoquinone (VIII) which shows no further traces of contamination in contrast to the experiment above. The so recovered 1,4-benzoquinone (VIII) can be applied again in a next reaction without further loss. Furthermore, the presence of the unwanted dialkylated byproducts could also be significantly reduced by this process.

Example 3: Synthesis of 2-methoxymethyl-p-phenylenediamine (I) with p-phenylenediamine (XI) as a By-Product (1) Synthesis of 2-methoxymethyl-1,4-benzochinone (IV)

A three necked flask was fitted with a reflux condenser and a thermometer and is charged with 1 eq.=3 g (27.5 mmol) 1,4-benzoquinone (VIII), 1.5 eq=3.71 g (41.2 mmol) 2-methoxyacetic acid (IX) in the presence of 0.3 eq.=1.41 g (8.24 mmol) silver nitrate and water (98 mL). The mixture was stirred and heated to 65° C. until complete dissolution was observed. The aqueous phase is floated continuously with a pump to avoid and sublimation of 1,4-benzoquinone (VIII) on the top of the flask. Then a solution of ammonium peroxodisulphate as radical former, 1.05 eq=6.72 g (28.8 mmol) in water was slowly, time-controlled, added at rate of 10 mL/h using a syringe driver or a pump (dosimat). Throughout addition, the reaction mixture is maintained at 65° C. After the addition is completed, the mixture is stirred for further 15 min. at 65° C. After cooling to room temperature, methylene chloride was added (130 mL). The formed layers were separated and the aqueous layer was extracted again 3 times with methylene chloride (100 ml each). The combined organic layers were dried over $Na_2SO_4$, filtered and concentrated under reduced pressure at room temperature in the dark. The residue may be purified by column chromatography on silica gel with pentane/methylene chloride, diethyl ether to obtain 2-methoxymethyl-1,4-benzochinone (IV) as an orange solid. Silver recovery can be done as disclosed in example 1.

(2) Conversion of (IV) and (VIII) to the bis-oxime Derivatives (Vb) and (Xb)

A three necked flask is charged with 1.23 g (15.00 mmol) sodium acetate and 2 g (13.15 mmol based on 2-methoxymethyl-1,4-benzochinone) crude mixture obtained from step (1). This mixture contains 2-methoxymethyl-1,4-benzochinone (IV), some dialkylated species and almost equivalent, the unreacted 1,4-benzoquinone (VIII). The mixture was dissolved in 50 mL Ethanol and heated to reflux for 12 h until all starting materials are consumed (qualitatively by TLC). The mixture is filtered hot and the ethanol removed under reduced pressure. The so obtained crude material is not purified but used instantly for the next step.

(3) Conversion of (Vb) and (Xb) to the bis-nitroso Derivatives (XII) and (XIII)

1.5 g (8.24 mmol based on 2-(methoxymethyl)-cyclohexa-2,5-diene-1,4-dione oxime) crude mixture obtained from step (2), containing 2-(methoxymethyl)-cyclohexa-2,5-diene-1,4-dione oxime (Vb) and cyclohexa-2,5-diene-1,4-dione oxime (Xb) and still traces of dialkylated bis oxime byproducts, are dissolved in 10 mL distilled water and heated to 55° C. Then 6.57 g (1.9 equiv.) 30% hydrogen chloride solution (15.65 mmol) is slowly added. 1.35 g (0.9 equiv.) 30% hydrogen peroxide solution (9.80 mmol) is slowly added time and temperature controlled within 30 min. The formed residue is collected by vacuum filtration, washed with water and dried to yield 1.45 g (8.05 mmol) =97.6% of a crude mixture containing 2-(methoxymethyl)-1,4-dinitroso-benzene and 1,4-dinitrosobenzene. The greenish yellow crystal mass is then distilled in vacuum (0.02 hPa) at temperatures between 80-160° C. to separate the fractions to isolate 0.68 g 2-(methoxymethyl)-1,4-dinitroso-benzene (XII) which corresponds to a 46.7% yield for this step. Since the yield calculation is based on the crude reaction mixture, the actual yield is somewhat higher. The second desired intermediate 1,4-dinitroso-benzene (XIII) is obtained in a similar yield, resulting in an approximately quantitative overall yield for intermediates (XII) and (XIII).

(4) Hydrogenation to 2-methoxymethyl-p-phenylenediamine (I) and p-phenylenediamine (XI)

0.60 g (3.33 mmol) 2-(methoxymethyl)-1,4-dinitroso-benzene (XII) and water moistured catalyst PD/C 10% (5% by weight) water-moisturedcatalyst Pd/C 10% (5% by weight; showing a water content of about 50% by weight; to note: catalyst must not show an acidic pH-value, if suspended in water; otherwise it should be treated with a base in advance and filtrated before use) are suspended in ethylacetate or methanol (ca. 8 parts by volume) and transferred under an inert atmosphere into a pressure vessel which has been evacuated and flooded with nitrogen. For safety reasons the vessel is again evacuated and flooded with nitrogen and finally charged with hydrogen up to a pressure of approx. 2 bar absolute. The hydrogenation starts in the presence of hydrogen after switching on the stirrer. At the same time the cooling of the reaction mixture is started. The cooling is controlled in such a way, that the reaction temperature is kept at approx. 20° C. At room temperature the take-up of hydrogen is moderate. The end of the hydrogen consumption appears from falling reaction temperature and decreasing take-up of hydrogen. To complete the conversion the reaction mixture is stirred further at room temperature for an additional period of 30 min. Then the reaction mixture is filtered under an inert atmosphere (it is important to have the reaction temperature at room temperature to avoid the crystallization of the 2-methoxymethyl-p-phenylenediamine, with may occur at lower temperature). The catalyst residue is washed twice with ethaylacetate or methanol (1 part by volume). After cooling the crude product precipitaes. Further recrystallization from toluene yields 0.45 g (2.96 mmol)=88.8% pure 2-methoxymethyl-p-phenylenediamine.

The hydrogenation of the cyclohexa-2,5-diene-1,4-dione oxime (XIII) as separated in step (2) can be done accordingly to the procedure described above to yield the commercially important p-phenylene diamine (XI) in comparable yield.

Example 4: Synthesis of 2-methoxymethyl-1,4-benzochinone (IV) Using 3-(hydroxymethyl)phenol (XIX) as Starting Material (1) Synthesis of 3-(methoxymethyl)-phenol (XX)

A pressurized reaction vessel is charged with 5 g (40.00 mmol) 3-(hydroxymethyl)phenol (XIX) followed by addition of 5.67 g (45.00 mmol) dimethylsulphate. This mixture is dissolved in 50 mL Methanol. Then 2 eq conc. sulphuric acid was slowly added at room temperature. After the addition of sulphuric acid is complete, the reaction mixture is heated in the sealed vessel at 150° C. for 4 hours. After cooling to room temperature, the solvent is evaporated in vacuum and the reaction mixture distilled to obtain 3.22 g (23.20 mmol) of 3-(methoxymethyl)-phenol (XX) in 58% yield as a colorless liquid.

(2) Oxidation of (XX) to form 2-methoxymethyl-1,4-benzochinone (IV)

a) Preparation of 2-methoxymethyl-1,4-benzochinone (IV)

The titanium superoxide catalyst was prepared according to literature standard. To a solution of titanium isoproyloxide (1 eq. 5.26 mL, 17.6 mmol) in 50 mL anhydrous methanol, was added, dropwise, over 40 min. at room temperature and under inert atmosphere, aq. 50% hydrogen peroxide solution (5.98 g, 175.00 mmol). After the addition of hydrogen peroxide is completed, the reaction mixture is stirred at room temperature for 45 min.

The yellow precipitate which was formed was collected by vacuum filtration, washed with cold methanol and dried in vacuum to obtain 2.25 g (quantitative conversion of titanium starting material) titanium superoxide catalyst.

To a solution of 3.00 g (23.96 mmol) 3-(methoxymethyl)-phenol (XX) in 40 mL ethanol, 0.60 g (20% w/w) titanium superoxide catalyst was added. Then, 24.62 mL of an aq. 35% hydrogen peroxide solution (12 eq., 287.52 mmol) was added slowly within 1 hour at room temperature under inert atmosphere in the dark under cooling to prevent the mixture from heating above room temperature. Elevated temperatures may cause strong foaming of the mixture due to degradation of hydrogen peroxide.

After the addition was completed, the mixture is stirred for 2 hours until full conversion of the starting material. The reaction mixture was then diluted with a 1:1 mixture of water and methylenechloride. The formed layers were separated while the aqueous layer was extracted two times with methylenechloride. The combines organic layers were washed with 10% aq. sodium hydrogencarbonate and then two times with brine, dried and the solvent removed under reduce pressure (in the dark without heating). The obtained residue was recrystallized with a mixture of cyclohexane/ethyl acetate (4:1) to isolate 2.92 g (19.17 mmol) 2-methoxymethyl-1,4-benzochinone (IV) as a yellow solid in 80% yield.

The following embodiments further illustrate the present invention.

1. A process for preparing 2-methoxymethyl-p-phenylenediamine (I), a cosmetically acceptable salt thereof, or mixture thereof, the process comprising the steps of:
    (a) providing 2-methoxymethyl-1,4-benzochinone (IV);
    (b) condensing 2-methoxymethyl-1,4-benzochinone (IV) with an amine source NH2R1 to form 2-(methoxymethyl)-N1(R1),N4(R1)-cyclohexa-2,5-diene-1,4-diimine (Va); and
    (c) reacting 2-(methoxymethyl)-N1(R1),N4(R1)-cyclohexa-2,5-diene-1,4-diimine (Va) in the presence of a hydrogen source to form 2-methoxymethyl-p-phenylenediamine (I).
2. The process of embodiment 1, wherein moiety R1 of amine source NH2-R1 is selected from OH, NH2, linear or branched (C1-C6)alkyl which optionally may be substituted with OH, linear or branched (C1-C6) alkylene-(C5-C6)cycloalkyl and linear or branched (C1-C6)alkylbenzol,
3. The process of embodiment 1, wherein step (b) comprises condensing 2-methoxymethyl-1,4-benzochinone (IV) with hydroxylamine NH2OH to form bis-oxime 2-(methoxymethyl)-cyclohexa-2,5-diene-1,4-dione oxime (Vb), and wherein step (c) comprises reacting (Vb) to form (I).
4. The process of any of embodiments 1 to 3, wherein step (a) comprises:
    (a1) alkylating 1,4-benzoquinone (VIII) in the presence of 2-methoxyacetic acid (IX) to form a mixture of 2-methoxymethyl-1,4-benzochinone (IV) and 1,4-benzoquinone (VIII); and
    (a2) removing 1,4-benzoquinone (VIII).
5. The process of embodiment 4, wherein removing 1,4-benzoquinone (VIII) in step (a2) is carried out by water vapour distillation or short path distillation or thin-film evaporation.
6. The process of any of embodiments 1 to 3, wherein step (a) comprises:
    (a3) providing 2-methyl-1,4-benzochinone (II);
    (a4) brominating 2-methyl-1,4-benzochinone (II) to form 2-bromomethyl-1,4-benzochinone (II); and
    (a5) etherifying 2-bromomethyl-1,4-benzochinone (II) to form 2-methoxymethyl-1,4-benzochinone (IV).
7. The process of embodiment 6, wherein step (a5) is carried out in the presence of an oxidizing agent.
8. The process of any of embodiments 1 to 3, wherein step (a) comprises:
    (a6) providing 1,4-dimethoxy-2-methyl-benzene (VI);
    (a7) brominating 1,4-dimethoxy-2-methyl-benzene (VI) to form 2(bromomethyl)-1,4-dimethoxy-benzene (VIIa);
    (a8) etherifying 2(bromomethyl)-1,4-dimethoxy-benzene (VIIa) to form 1,4-dimethoxy-2-(methoxymethyl)benzene (VIIb); and (a9) oxidizing 1,4-dimethoxy-2-(methoxymethyl)benzene (VIIb) to form 2-methoxymethyl-1,4-benzochinone (IV).
9. The process of any of embodiments 1 to 3, wherein step (a) comprises:
   (a10) methylating 3-(hydroxymethyl)phenol (XIX) to form 3-(methoxymethyl)phenol (XX); and
   (a11) oxidizing 3-(methoxymethyl)phenol (XX) to form 2-methoxymethyl-1,4-benzochinone (IV).
10. The process of embodiment 9, wherein step (a11) is carried out using hydrogen peroxide H2O2 as an oxidizer.
11. The process of embodiment 9 or 10, wherein step (a11) is carried out in the presence of a catalyst.
12. The process of embodiment 11, wherein the catalyst is a metal catalyst.
13. The process of embodiment 12, wherein the catalyst is titanium superoxide.
14. The process of any of embodiments 9 to 12, wherein step (a10) is carried out in the presence of dimethylsulfate.
15. The process of any of the preceding embodiments, wherein step (b) is carried out in alcohol or an aqueous alcoholic solution.
16. The process of embodiment 15, wherein step (b) is carried out in ethanol.
17. The process of any of the preceding embodiments, wherein step (b) is carried out in the presence of an organic base.
18. The process of embodiment 17, wherein the organic base is selected from calcium carbonate, sodium carbonate, potassium carbonate, sodium acetate, DBU, DBN, Huenig Base, ammonium sulphate, sodium hydrogencarbonate and potassium hydrogencarbonate.
19. The process of any of the preceding embodiments, wherein the hydrogen source in step (c) is selected from hydrogen and hydrazine.
20. The process of any of the preceding embodiments, wherein step (c) is carried out in the presence of a catalyst.
21. The process of embodiment 20, wherein the catalyst is a metal catalyst.
22. The process of embodiment 21, wherein the metal catalyst is selected from the group consisting of Fe, Pd/C, Pd/(OH)$_2$, Raney-Ni, Pt/C, PtO$_2$, and mixtures thereof.
23. The process of any of the preceding embodiments, wherein the solvent in step (c) is selected from the group consisting of methanol, ethanol, ethylacetate, mixtures thereof, and aqueous solutions of methanol and/or ethanol.
24. The process of any of embodiments 1 to 3, comprising the steps:
   (a1) alkylating 1,4-benzoquinone (VIII) in the presence of 2-methoxyacetic acid (IX) to form a mixture of 2-methoxymethyl-1,4-benzochinone (IV) and 1,4-benzoquinone (VIII);
   (b1) in the mixture obtained in step (a1), condensing 2-methoxymethyl-1,4-benzochinone (IV) and 1,4-benzoquinone (VIII) with an amine source NH2R1 to form a mixture of 2-(methoxymethyl)-N1(R1),N4(R1)-cyclohexa-2,5-diene-1,4-diimine (Va) and N1(R1),N4(R1)-cyclohexa-2,5-diene-1,4-diimine (Xa);
   (b2) in the mixture obtained in step (b1), oxidizing 2-(methoxymethyl)-N1(R1),N4(R1)-cyclohexa-2,5-diene-1,4-diimine (Va) and N1(R1),N4(R1)-cyclohexa-2,5-diene-1,4-diimine (Xa) to form a mixture of 2-(methoxymethyl)-1,4-dinitroso-benzene (XII) and 1,4-dinitroso-benzene (XIII);
   (b3) isolating 2-(methoxymethyl)-1,4-dinitroso-benzene (XII), and isolating 1,4-dinitroso-benzene (XIII);
   (c1) reacting 2-(methoxymethyl)-1,4-dinitroso-benzene (XII) in the presence of a hydrogen source to form 2-methoxymethyl-p-phenylenediamine (I); and
   (c2) reacting 1,4-dinitroso-benzene (XIII) in the presence of a hydrogen source to form p-phenylenediamine (XI).
25. The process of embodiment 24, wherein moiety R1 of amine source NH2-R1 is selected from OH, NH2, linear or branched (C1-C6)alkyl which optionally may be substituted with OH, linear or branched (C1-C6)alkylene-(C5-C6)cycloalkyl and linear or branched (C1-C6)alkylbenzol.
26. The process of embodiment 24, wherein step (b1) comprises condensing 2-methoxymethyl-1,4-benzochinone (IV) and 1,4-benzoquinone (VIII) with hydroxylamine NH2OH to form a mixture of bis-oxime 2-(methoxymethyl)-cyclohexa-2,5-diene-1,4-dione oxime (Vb) and cyclohexa-2,5-diene-1,4-dione oxime (Xb), and wherein step (b2) comprises reacting a mixture of (Vb) and (Xb) to form a mixture of (XII) and (XIII).
27. The process of any of embodiments 24 to 26, wherein step (b1) is carried out in the presence of an organic base.
28. The process of embodiment 27, wherein the organic base is selected from calcium carbonate, sodium carbonate, potassium carbonate, sodium acetate, DBU, DBN, Huenig Base, ammonium sulphate, sodium hydrogencarbonate and potassium hydrogencarbonate.
29. The process of any of embodiments 24 to 28, wherein step (c1) and/or step (c2) is carried out in the presence of a catalyst.
30. The process of embodiment 29, wherein the catalyst is a metal catalyst.
31. The process of embodiment 30, wherein the metal catalyst is selected from the group consisting of Fe, Pd/C, Pd/(OH)$_2$, Raney-Ni, Pt/C, PtO$_2$, and mixtures thereof.
32. A process for preparing 2-methoxymethyl-p-phenylenediamine (I), a cosmetically acceptable salt thereof, or mixture thereof, the process comprising the steps of:
   (i) acylating p-hydrochinone (XIV) with methyl-chlorformiate to form methyl 2,5-dihydroxybenzoate (XV);
   (ii) oxidizing methyl 2,5-dihydroxybenzoate (XV) to form methyl 3,6-dioxocyclohexa-1,4-diene-1-carboxylate (XVI);
   (iii) condensing methyl 3,6-dioxocyclohexa-1,4-diene-1-carboxylate (XVI) with hydroxylamine NH2OH to form bis-oxime (3Z,6E)-3,6-bis(hydroxyimino)cyclohexa-1,4-diene-1-carboxylic acid (XVII);
   (iv) converting of bis-oxime (3Z,6E)-3,6-bis(hydroxyimino)cyclohexa-1,4-diene-1-carboxylic acid (XVII) into the corresponding thionoester (XVIII); and
   (v) hydrogenating thionoester (XVIII) in the presence of a hydrogen source to form 2-methoxymethyl-p-phenylenediamine (I).
33. The embodiment of claim 32, wherein step (v) is carried out in the presence of a catalyst.

34. The process of embodiment 33, wherein the catalyst is a metal catalyst.

35. The process of embodiment 34, wherein the metal catalyst is selected from the group consisting of Fe, Pd/C, Pd/(OH)$_2$, Raney-Ni, Pt/C, PtO$_2$, and mixtures thereof.

36. 2-Methoxymethyl-1,4-benzochinone (IV).

The invention claimed is:

1. A process for preparing 2-methoxymethyl-p-phenylene diamine (I), a cosmetically acceptable salt thereof, or mixture thereof, the process comprising the steps of:
   (a1) (a1) alkylating 1,4-benzoquinone (VIII) in the presence of 2-methoxyacetic acid (IX) to form a mixture of 2-methoxymethyl-1-4-benzochinone (IV) and 1,4-benzoquinone (VIII);
   (b1) condensing 2-methoxymethyl-1-4-benzochinone (IV) and 1,4-benzoquinone (VIII) with NH$_2$R1 to form a mixture of 2-(methoxymethyl)-N1(R1), N4(R1)-cyclohexa-2,5-diene-1,4-diimine (Va) and N1(R1), N4(R1)-cyclohexa-2,5-diene-1,4-diiminine (Xa) wherein moiety R1 of NH$_2$R1 is selected from OH, NH2, linear or branched (C1-C6)alkyl which optionally may be substituted with OH, linear or branched (C1-C6)alkylene-(C5-C6) cycloalkyl and linear or branched (C1-C6)alkyl benzol;
   (b2) in the mixture obtained in step (b1), oxidizing 2-(methoxymethyl)-N1(R1), N4(R1)-cyclohexa-2,5-diene-1,4-diimine (Va) and N1(R1), N4(R1)-cyclohexa-2,5-diene-1,4-diiminine (Xa); to form a mixture of 2-(methoxymethyl)-1,4-dinitroso-benzene (XII) and 1,4-dinitrosobenzene (XIII);
   (b3) isolating 2-(methoxymethyl)-1,4-dinitroso-benzene (XII) and 1,4-dinitrosobenzene (XIII);
   (c1) reacting 2-(methoxymethyl)-1,4-dinitroso-benzene (XII) in the presence of a hydrogen source to form 2-methoxymethyl-P-phenylene diamine (I) and
   (c2) reacting 1,4-dinitroso-benzene (XIII) in the presence of a hydrogen source to form p-phenylene diamine(XI).

2. The process of claim 1 wherein step (b1) comprises condensing 2-methoxymethyl-1,4 benzochinone (IV) and 1,4)-benzoquinone (VIII) with hydroxyamine NH2OH to form a mixture of bis-oxime 1-(methoxymethyl)-cyclohexa-2,5-diene-1,4-dione oxime (Vb) and cyclohexa-2,5-diene-1,4-dione oxime (Xb), and wherein step (b2) comprises reacting a mixture of (Vb) and (Xb) to form a mixture of (XII) and XIII).

3. The process of claim 1, wherein step (ci) and/or step (c2) is carried out in the presence of a catalyst selected from the group consisting of Fe, Pd/C, Pd(OH)$_2$, Raney-Ni, Pt/C, PtO$_2$ and mixtures thereof.

4. The process of claim 1 wherein the isolation of 2-(methoxymethyl)-1,4-dinitroso-benzene (XII) and 1,4-dinitrosobenzene (XIII) in step (b3) separates 2-(methoxymethyl)-1,4-dinitroso-benzene (XII) from 1,4-dinitrosobenzene (XIII).

* * * * *